(12) United States Patent
Vogt et al.

(10) Patent No.: US 11,066,398 B2
(45) Date of Patent: Jul. 20, 2021

(54) SMALL MOLECULE C-MYC INHIBITORS

(71) Applicants: THE SCRIPPS RESEARCH INSTITUTE, La Jolla, CA (US); SORRENTO THERAPEUTICS, San Diego, CA (US); Peter K. Vogt, La Jolla, CA (US); Francis X. Tavares, Durham, NC (US); Kim D. Janda, La Jolla, CA (US)

(72) Inventors: Peter K. Vogt, La Jolla, CA (US); Francis X. Tavares, Durham, NC (US); Kim D. Janda, La Jolla, CA (US)

(73) Assignees: The Scripps Research Institute, La Jolla, CA (US); Sorrento Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/035,842

(22) PCT Filed: Dec. 10, 2014

(86) PCT No.: PCT/US2014/069533
§ 371 (c)(1),
(2) Date: May 11, 2016

(87) PCT Pub. No.: WO2015/089180
PCT Pub. Date: Jun. 18, 2015

(65) Prior Publication Data
US 2016/0264560 A1    Sep. 15, 2016

Related U.S. Application Data

(60) Provisional application No. 61/914,590, filed on Dec. 11, 2013.

(51) Int. Cl.
| | |
|---|---|
| *C07D 405/04* | (2006.01) |
| *C07D 213/56* | (2006.01) |
| *C07D 213/74* | (2006.01) |
| *C07D 413/04* | (2006.01) |
| *C07D 401/04* | (2006.01) |
| *A61P 35/00* | (2006.01) |
| *A61K 31/4418* | (2006.01) |
| *A61K 31/44* | (2006.01) |
| *C07D 413/14* | (2006.01) |
| *C07D 405/14* | (2006.01) |

(52) U.S. Cl.
CPC ............ *C07D 413/14* (2013.01); *A61K 31/44* (2013.01); *A61K 31/4418* (2013.01); *A61P 35/00* (2018.01); *C07D 213/56* (2013.01); *C07D 213/74* (2013.01); *C07D 401/04* (2013.01); *C07D 405/04* (2013.01); *C07D 405/14* (2013.01); *C07D 413/04* (2013.01)

(58) Field of Classification Search
CPC .. C07D 213/56; C07D 413/14; C07D 213/74; C07D 401/04; C07D 405/04; C07D 405/14; C07D 413/04; A61P 35/00; A61K 31/44; A61K 31/4418
See application file for complete search history.

(56) References Cited

PUBLICATIONS

Fujimori et al. J. Comb. Chem. 2003, 5, pp. 625-631.*
Zhao et al. 2004, Bioorganic and Medicinal Chemistry Letters, 14, pp. 1333-1337.*
Basnet et al. 2007, Bioorganic and Medicinal Chemistry, 15, pp. 4351-4359.*
Covell et al. 2007, Mol. Cancer Ther., 6(8), pp. 2261-2270.*
Zhao et al. 2001, Bioorganic and Medicinal Chemistry Letters, pp. 2659-2662.*
Neves et al. 2009, J. Med. Chem. 52, pp. 143-150.*
Jiang et al. 2009, Biometals, 22, pp. 297-305.*
Jeong et al. 2011, Bull. Korean Chem. Soc., vol. 32, No. 10, pp. 3566-3570.*
Yao et al. Jul. 8, 2013, Z. Kristallogr., 228, pp. 323-329.*

* cited by examiner

*Primary Examiner* — Kara R McMillian
(74) *Attorney, Agent, or Firm* — Hugh Wang; Thomas Fitting

(57) ABSTRACT

This invention provides small molecule Myc-inhibitors. Also provided in the invention are therapeutic applications of these compounds for treating Myc-driven cancer and other related methods.

1 Claim, 9 Drawing Sheets

Daudi

K562

HFF

Daudi

K562

HFF

SMALL MOLECULE C-MYC INHIBITORS

CROSS-REFERENCE TO RELATED APPLICATIONS

The subject patent application claims the benefit of priority to U.S. Provisional Patent Application No. 61/914,590 (filed Dec. 11, 2013). The full disclosure of the priority application is incorporated herein by reference in its entirety and for all purposes.

STATEMENT OF GOVERNMENT LICENSE RIGHTS

This invention was made with government support under grant number CA078230 awarded by the National Institutes of Health. The government has certain rights in the invention.

TECHNICAL FIELD

The present disclosure provides a genus of compounds that are c-Myc inhibitors. The present disclosure further provides methods for treating tumors comprising administering an effective amount of a disclosed c-Myc inhibitor.

BACKGROUND OF THE INVENTION

The proto-oncogene c-myc encodes a transcription factor (Myc) that controls cell proliferation. Myc also plays a role in regulating cell cycle, cell growth, angiogenesis, apoptosis, and oncogenesis. Myc is involved in almost all cancers, and a gain of function in Myc is seen in nearly all human cancers. Myc's activity can increase in tumors as a consequence of mutations, chromosomal rearrangements, increased expression, or gene amplification. levated or deregulated expression of c-Myc has been detected in a wide range of human cancers and is often associated with aggressive, poorly differentiated tumors. Such cancers include colon, breast, cervical, small cell lung carcinomas, osteosarcomas, glioblastomas, melanoma and myeloid leukemias.

Because of its broad pathogenic significance, Myc is an important cancer target. However, Myc has been challenging target for small molecule inhibitors. Both conceptual and practical difficulties have stood in the way of identifying potent and effective small molecular inhibitors of Myc. The conceptual obstacles reflect concern about inhibiting a gene that controls essential cellular activities. The main practical difficulty in targeting Myc is the absence of pockets or grooves that could serve as binding sites for small molecules. Small molecule Myc-inhibitors known in the art lack the potency and appropriate pharmacokinetic properties for in vivo applications.

There is a need in the art for better means for inhibiting c-Myc mediated oncogenic activities and signaling pathways, as well as more effective therapies for treating and preventing cancers. The present disclosure addresses this and other unfulfilled needs in the art.

SUMMARY OF THE INVENTION

In one aspect, the present disclosure provides a compound having a structure from Formula 1:

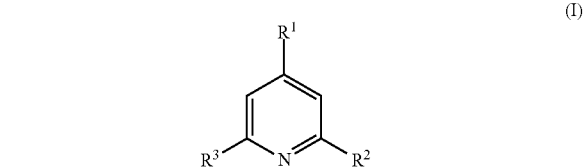

wherein each of $R^1$, $R^2$ and $R^3$ is independently selected from the group consisting of furan-2-yl, furan-3-yl, furan-4-yl, 4-halobenzyl, 3-halobenzyl, 5-halobenzyl, dihalobenzyl, trihalobenzyl, tetrahalobenzyl, pentahalobenzyl,

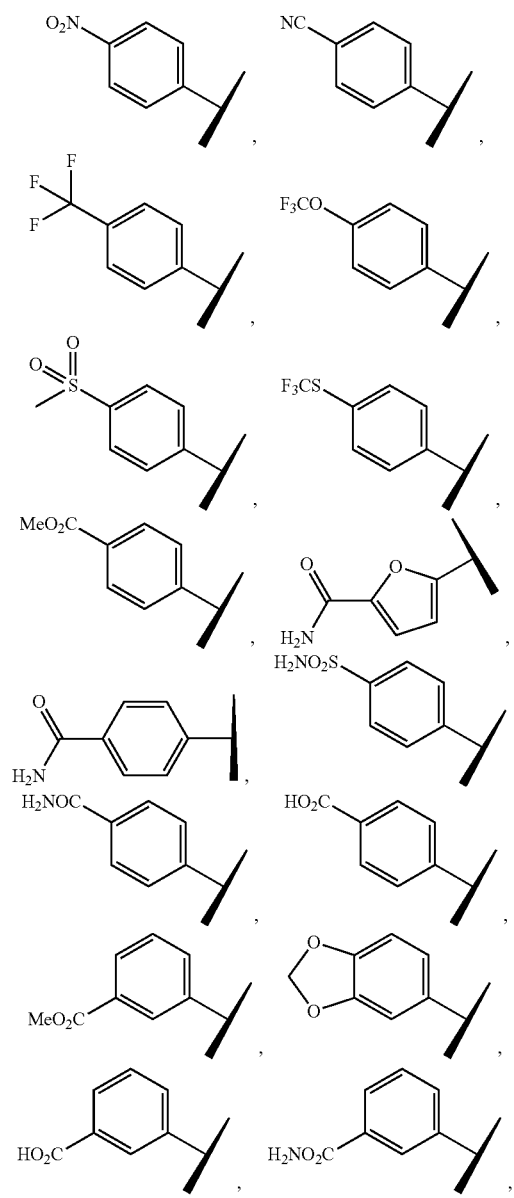

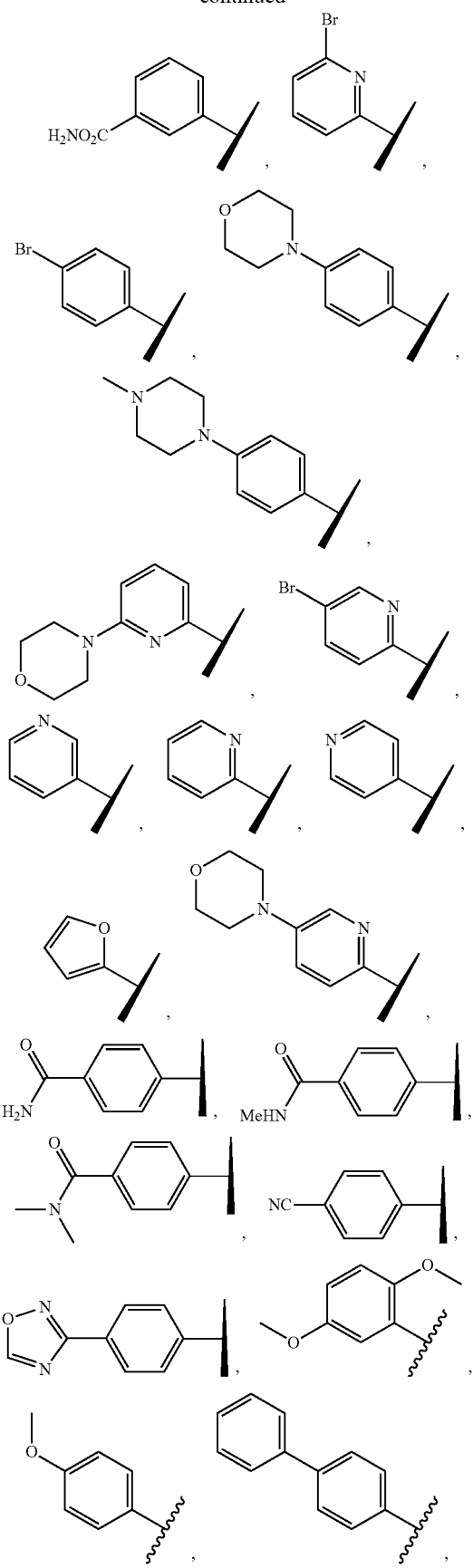
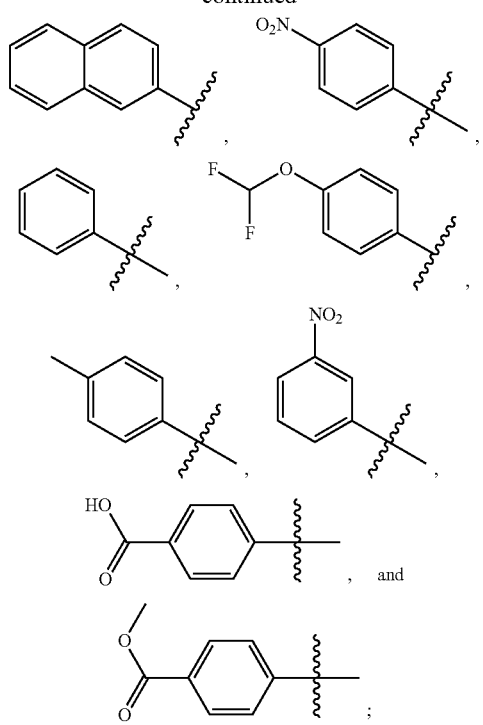
wherein halo is fluoro, chloro, bromo or iodo; and with the proviso that when $R^3$ is furanyl, $R^1$ cannot be
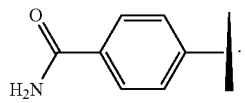
Preferably, $R^1$ is
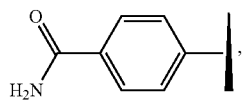
$R^3$ is
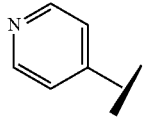
or a furanyl, and $R^2$ is selected from the group consisting of
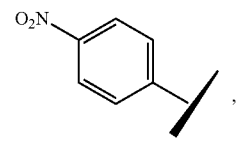

furanyl,

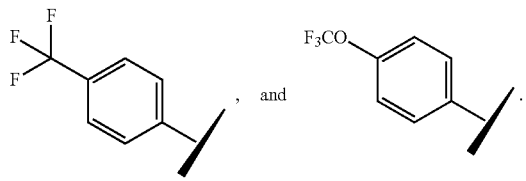

The present disclosure further provides a pharmaceutical composition for treating cancer, comprising a compound having a structure from Formula 1:

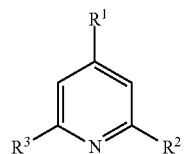
(I)

wherein each of $R^1$, $R^2$ and $R^3$ is independently selected from the group consisting of furan-2-yl, furan-3-yl, furan-4-yl, 4-halobenzyl, 3-halobenzyl, 5-halobenzyl, dihalobenzyl, trihalobenzyl, tetrahalobenzyl, pentahalobenzyl,

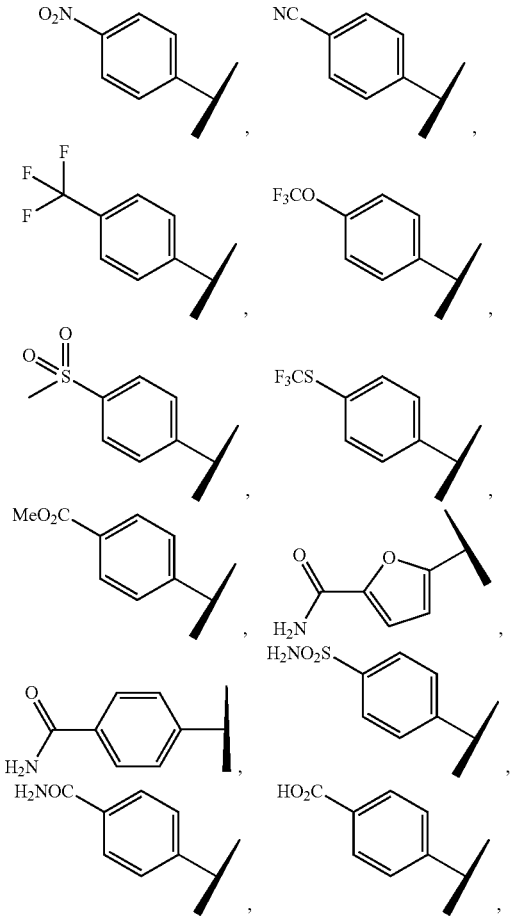

-continued

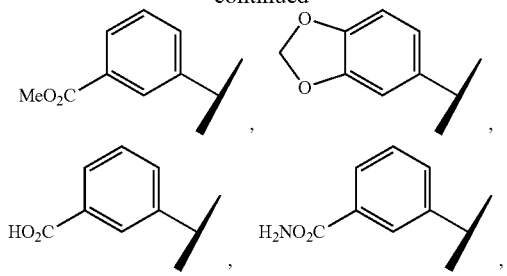

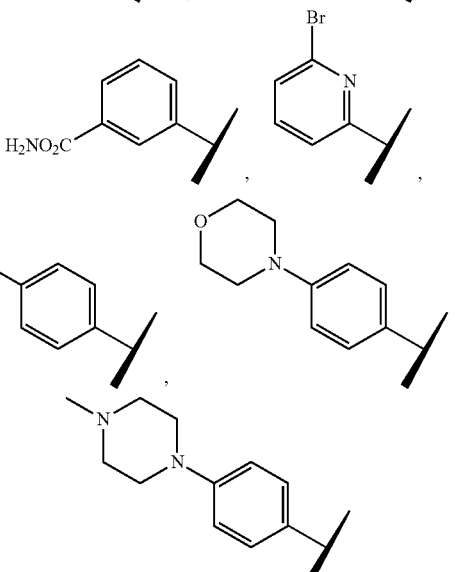

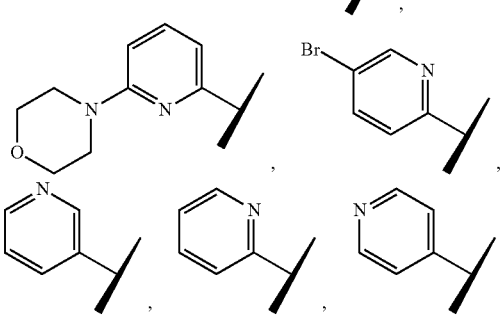

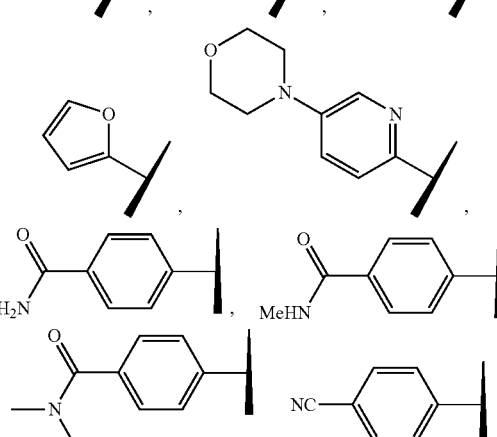

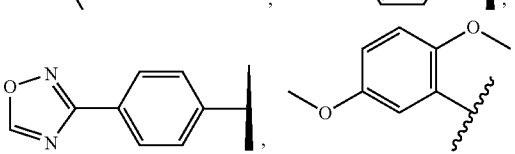

-continued

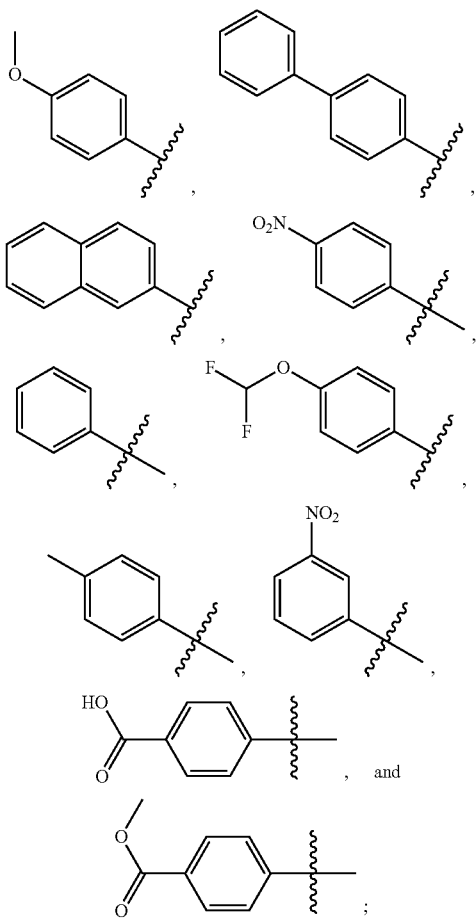

wherein halo is fluoro, chloro, bromo or iodo.

Preferably, $R^1$ is

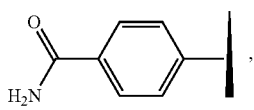

$R^3$ is

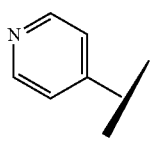

or a furanyl, and $R^2$ is selected from the group consisting of

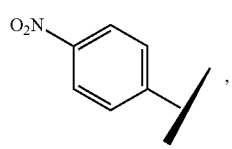

furanyl,

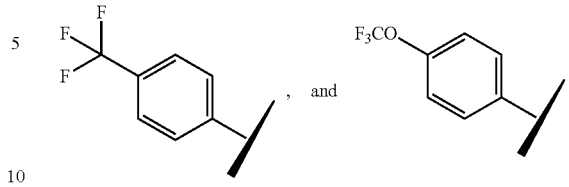

The present disclosure further provides a method for treating cancers, comprising administering an effective amount of a compound having a structure from Formula 1:

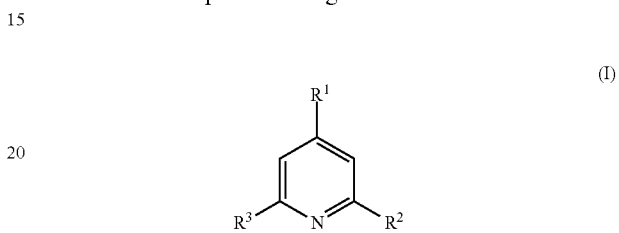

(I)

wherein each of $R^1$, $R^2$ and $R^3$ is independently selected from the group consisting of furan-2-yl, furan-3-yl, furan-4-yl, 4-halobenzyl, 3-halobenzyl, 5-halobenzyl, dihalobenzyl, trihalobenzyl, tetrahalobenzyl, pentahalobenzyl,

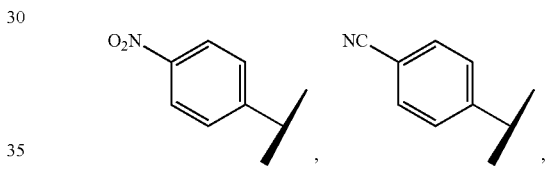

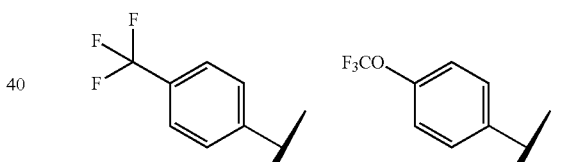

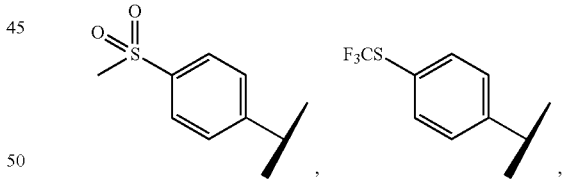

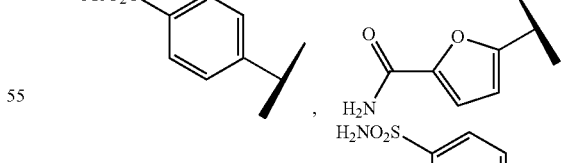

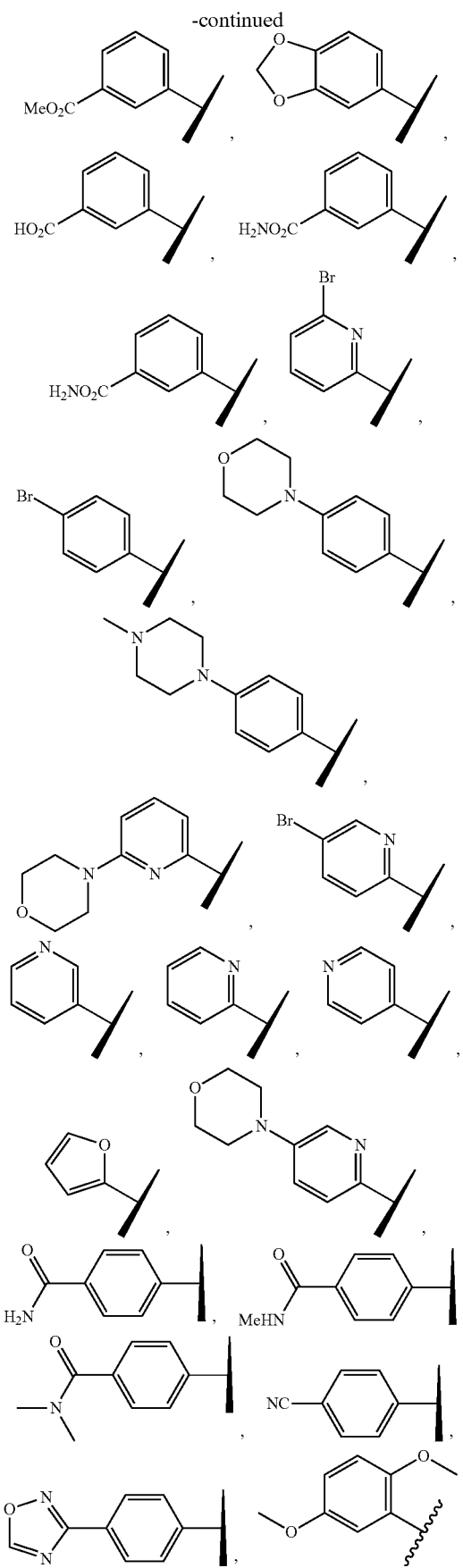
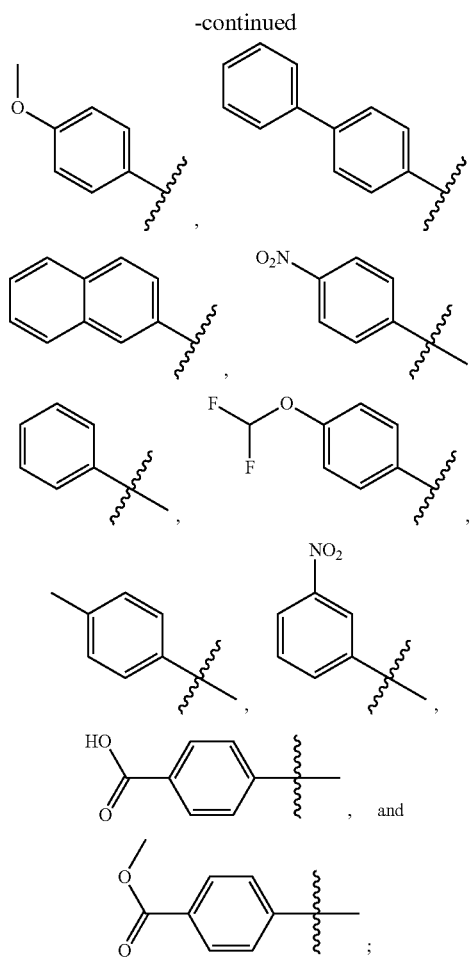
wherein halo is fluoro, chloro, bromo or iodo.
Preferably, $R^1$ is
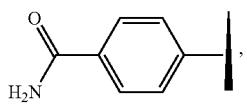
$R^3$ is
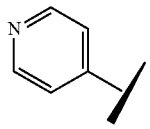
or a furanyl, and $R^2$ is selected from the group consisting of
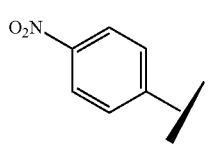

furanyl,

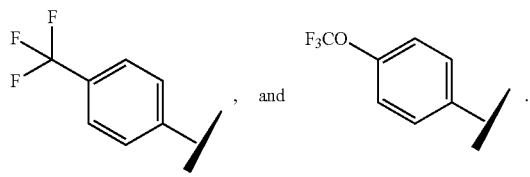

Additional aspects and embodiments of the invention, as well as the specific properties and advantages of the present invention, are described in the remaining portions of this patent specification and the attached claims.

DESCRIPTION OF THE DRAWINGS

FIG. 8C shows the non-specific cytotoxicity of the compounds, as tested in Human Foreskin Fibroblasts (HFF).

FIG. 9C shows the non-specific cytotoxicity of the compounds, as tested in HFF.

DETAILED DESCRIPTION

I. Overview

The invention relates to c-Myc-inhibiting compounds and their uses in inhibiting c-Myc signaling pathway and in treating cancers. Myc is a transcriptional regulator that belongs to a family of basic helix-loop-helix leucine zipper (bHLH-LZ) proteins that dimerize with the bHLH-LZ protein MAX to become functional. The MYC-MAX heterodimer preferentially binds to the E-Box motif, a palindromic DNA sequence. MYC affects transcription at two molecular levels. As a transcription factor, it can bind to the promoters of target genes to stimulate or repress transcriptional activity. As an amplifier of transcription in cancer cells that show MYC gain of function, it enhances the activity of existing transcriptional programs. In both situations, MYC must dimerize with MAX to be effective. The human genome contains three MYC genes and corresponding proteins, c-MYC, N-MYC and L-MYC. Unless otherwise noted, MYC is used herein to indicate the c-MYC protein. c-Myc can also act as a transcriptional repressor. By binding Miz-1 transcription factor and displacing the p300 co-activator, it inhibits expression of Miz-1 target genes. In addition, Myc has a direct role in the control of DNA replication.

Myc is activated upon various mitogenic signals such as Wnt, Shh and EGF (via the MAPK/ERK pathway). By modifying the expression of its target genes, Myc activation results in numerous biological effects. The first to be discovered was its capability to drive cell proliferation (upregulates cyclins, downregulates p21), but it also plays a very important role in regulating cell growth (upregulates ribosomal RNA and proteins), apoptosis (downregulates Bcl-2), differentiation and stem cell self-renewal. Myc is a very strong proto-oncogene and it is very often found to be upregulated in many types of cancers. Myc overexpression stimulates gene amplification, presumably through DNA over-replication. As used herein, c-Myc signaling pathway or c-Myc mediated cellular activity refers to any biochemical effect or cellular response that will occur as a result of activation of Myc.

In summary, c-Myc drives a variety of pro-growth and anti-apoptotic genes, and is frequently overexpressed in cancer. Accordingly, inhibition of oncogenic transformation caused by c-Myc would represent a potent chemotherapeutic strategy with wide ranging utility in treating both solid tumors and leukemia. The present invention provides a genus of compounds that inhibit MYC-MAX interaction and are thus able to treat a wide spectrum of cancers. The invention also provides methods for employing the Myc inhibitor compounds described herein and derivative compounds in various therapeutic applications.

II. c-Myc Inhibitor Compounds

Figure 1:
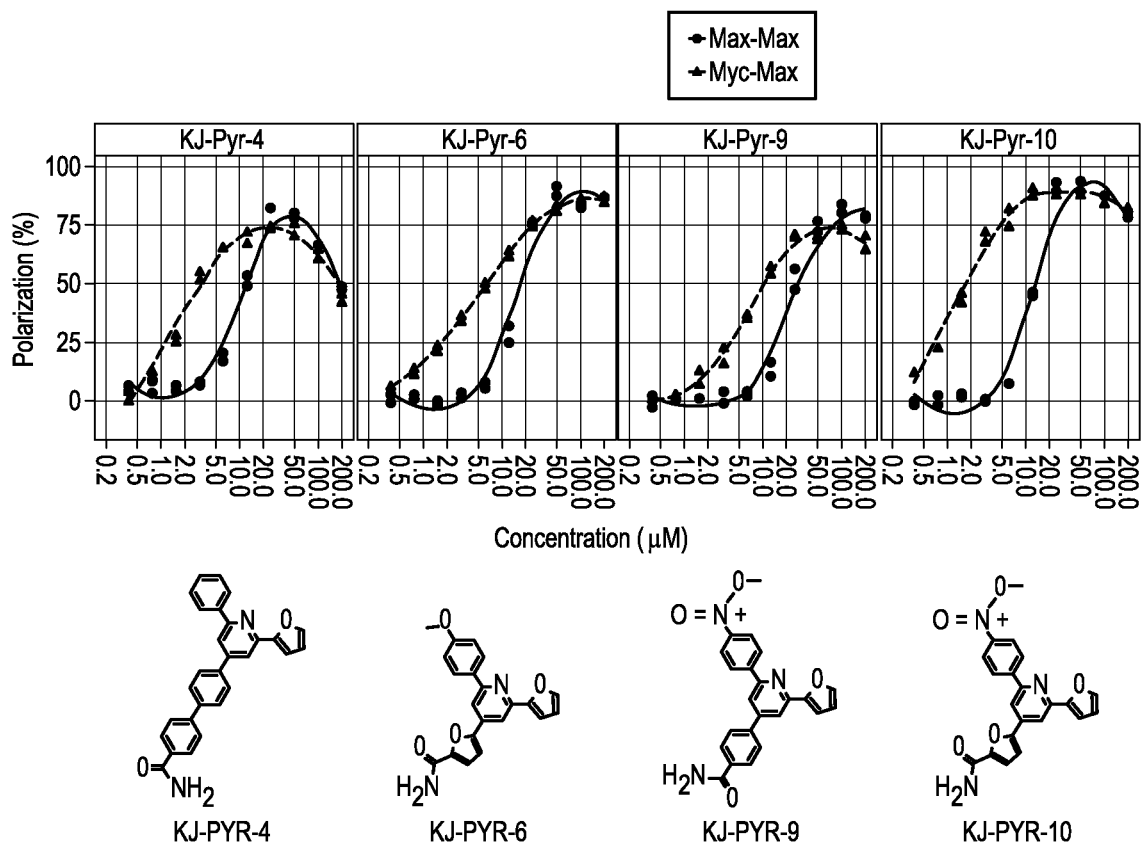
FIG. 1 shows that KJ-Pyr-9 prevents Myc-dependent transformation of primary cells by Avian retroviruses. Chicken embryonic fibroblasts were infected with $10^2$, $10^3$, or $10^4$-fold dilutions of an Avian virus containing Myc (RCAS(A)-ATG-Myc). The cells were overlaid with nutrient agar media and maintained for 10 days. Top: Fluorescence polarization data of KJ-Pyr-4, KJ-Pyr-6, KJ-Pyr-9 and KJ-Pyr-10, comparing binding to MYC-MAX with the interaction with MAX-MAX. Bottom: Structures of the four compounds.

As detailed in the Examples below, the invention is predicated in part on the discovery by the present inventors of c-Myc inhibiting activities of several known compounds. These compounds were from a combinatorial library of Kröhnke pyridine compounds initially prepared for solution-phase biological screening (Fujimori et al., J. Combinatorial Chem. 5:627-631, 2003). The novel c-Myc inhibiting activities of some of the compounds were identified through a fluorescence polarization screen for MYC-MAX interaction. The identified compounds are able to inhibit Myc-induced oncogenic transformation in cell culture, interfere with the proliferation of Myc-overexpressing human and avian cells, and reduce Myc-mediated transcriptional regulation. In addition, the compounds can effectively block the growth of a xenotransplant of Myc-overexpressing human cancer cells. The specific Myc-inhibitor compounds exemplified herein are 4-(2-(furan-2-yl)-6-(4-nitrophenyl)pyridin-4-yl)benzamide (KJ-Pyr-9), 5-(2-(furan-2-yl)-6-(4-nitrophenyl)pyridin-4-yl)furan-2-carboxamide (KJ-Pyr-10), 5-(2-(furan-2-yl)-6-(4-methoxyphenyl)pyridin-4-yl)furan-2-carboxamide (KJ-Pyr-6), 4'-(2-(furan-2-yl)-6-phenylpyridin-4-yl)-[1,1'-biphenyl]-4-carboxamide (KJ-Pyr-4). Their structures are shown in FIG. 1.

In addition to the c-Myc inhibitor compounds exemplified herein, derivative compounds that can be modified and synthesized from these compounds can also be suitable for the practice of the methods of the invention. Some specific c-Myc inhibitor compounds derived from these known compounds are described in detail below. For example, relative to KJ-Pyr-9, 10, 6 or 4, some of their derivative compounds can have one or more mono- or multi-valent groups replaced with a different mono- or multi-valent group. The replaced group can be, e.g., H; halogen; straight, cyclic or branched chain alkyl; straight, cyclic or branched chain alkenyl; straight, cyclic or branched chain alkynyl; halo-alkyl, -alkenyl or -alkynyl; CN; CF$_3$; aryl and substituted aryl groups in which any or all H groups of the aryl ring is substituted with a different group; heterocyclic and substituted heterocyclic groups in which any or all groups of the aryl ring is substituted with a different group; carboxyl; carbonyl; alkoxyl; alkyloxyalkanes; alkoxycarbonyl; aryloxyl, heterocyclyloxyl; hydroxyl; amine; amide; amino; quaternary amino; nitro; sulfonyl; alkylamine; silyl, siloxyl; saturated C—C bonds; unsaturated C—C bonds; ester, ether, amino; amide, urethane, carbonyl, acetyl and ketyl groups; hetero atoms, including N, S and O; polymer groups; and amino acids. In some derivative compounds, one or more hydrogens can be substituted with a lower alkyl group. The various derivative compounds can be subject to a functional test (e.g., proliferation inhibition assay as exemplified herein) to ascertain their c-Myc inhibiting activities.

In some embodiments, variants or derivative compounds with similar or improved properties can be obtained by rational optimization of the exemplified c-Myc inhibitor compounds (the lead compounds). Optionally, the compounds generated via rational design can be further subjected to a functional test or screening in order to identify compounds with improved activities. Detailed methods for designing and screening such variant compounds are described below. The various c-Myc inhibitor compounds exemplified herein and their variants or derivatives can all be readily prepared using routinely practiced methods of organic chemistry or the protocols described herein or in Fujimori et al., J. Combinatorial Chem. 5:627-631, 2003.

In one aspect, the invention provides methods for identifying an inhibitor of c-Myc signaling pathway with improved properties. The methods involve (a) synthesizing one or more structural analogs of a lead c-Myc inhibitor compound selected from the group consisting of 4-(2-(furan-2-yl)-6-(4-nitrophenyl)pyridin-4-yl)benzamide (KJ-Pyr-9), 5-(2-(furan-2-yl)-6-(4-nitrophenyl)pyridin-4-yl)furan-2-carboxamide (KJ-Pyr-10), 5-(2-(furan-2-yl)-6-(4-methoxyphenyl)pyridin-4-yl)furan-2-carboxamide (KJ-Pyr-6), and 4'-(2-(furan-2-yl)-6-phenylpyridin-4-yl)-[1,1'-biphenyl]-4-carboxamide (KJ-Pyr-4), and (b) performing a functional assay on the analogs to identify an analog that has an improved biological or pharmaceutical property relative to that of the lead inhibitor compound. In some preferred methods, the employed lead c-Myc inhibitor compound is 4-(2-(furan-2-yl)-6-(4-nitrophenyl)pyridin-4-yl)benzamide (KJ-Pyr-9) or 5-(2-(furan-2-yl)-6-(4-nitrophenyl)pyridin-4-yl)furan-2-carboxamide (KJ-Pyr-10). The improved biological or pharmaceutical property to be screened for can be, e.g., an enhanced activity in inhibiting c-Myc mediated signaling activities. Alternatively, the improved biological or pharmaceutical property can be an enhanced activity in inhibiting growth of a tumor cell, e.g., enhanced inhibitory activity on growth of colon cancer, breast cancer, cervical cancer, a small cell lung carcinoma, an osteosarcoma, a glioblastoma, melanoma, or a myeloid leukemia.

As exemplification, synthesis and activities of a number of analogs or variant compounds derived from the above known compounds are described below.

III. Synthesis Scheme and Activities of Some Exemplified c-Myc Inhibitor Compounds The following table shows exemplary structures that have been synthesized and assayed with assay data indicated, along with their code names.

| | R | Activity Myc/Max | Cytotox (cancer) | Cytotox (control) |
|---|---|---|---|---|
| CG-RS-44 | O$_2$N–⟨phenyl⟩– | +++ | – | +++/+ |

-continued
| | | | | |
|---|---|---|---|---|
| CG-RS-50 | 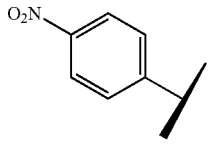 | + | + | +++ |
| CG-RS-47 | 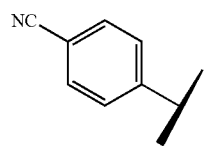 | +++ | ++ | ++/− |
| CG-RS-54 | 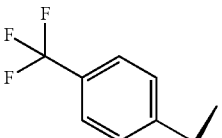 | + | +++ | + |
| CG-RS-55 | 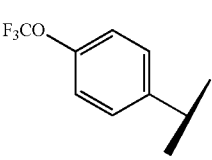 | + | +++ | + |
| CG-RS-58 | 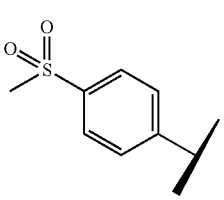 | − | ++ | +++ |
| CG-RS-61 | 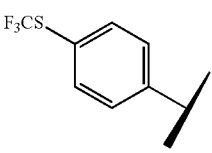 | − | + | + |
| CG-RS-64 | 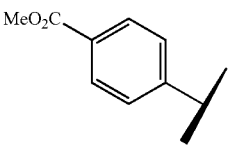 | − | + | + |
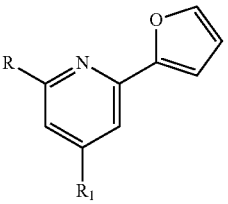
$R_1 =$ 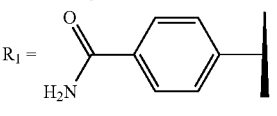
$R_{1\ (CG\text{-}RS\text{-}50)} =$ 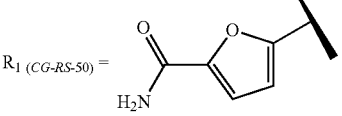

-continued
| | | | | |
|---|---|---|---|---|
| CG-RS-66 | 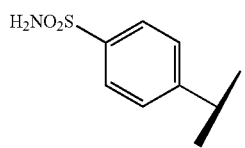 | + | ++ | +++/− |
| CG-RS-67A | 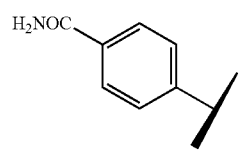 | | | |
| CG-RS-67B | 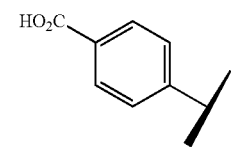 | | | |
| CG-RS-70 | 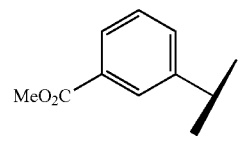 | +++ | | + |
| CG-RS-72 | 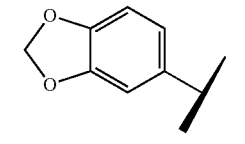 | | | |
| CG-RS-73(B) | 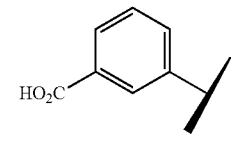 | | | |
| CG-RS-75 | 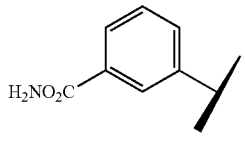 | | | |
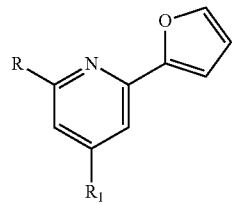
$R_1 =$ 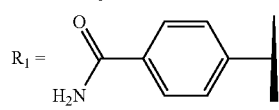
| | | | | |
|---|---|---|---|---|
| CG-RS-91 |  | − | − | − |

|  |  | | | |
|---|---|---|---|---|
| CG-RS-106 | 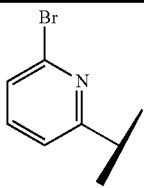 | – | | |
| CG-RS-90 | 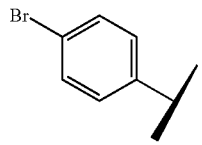 | – | – | +++ |
| CG-RS-116 | 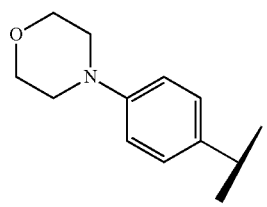 | | | |
| CG-RS-109 | 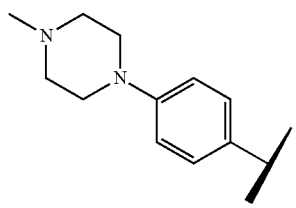 | | | |
| CG-RS-115 | 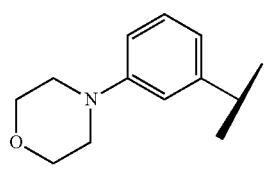 | | | |
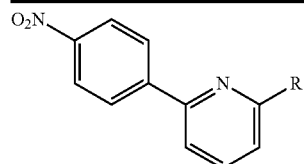
R₁ = 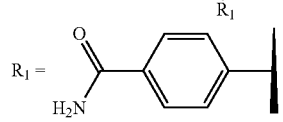
|  | R | R1 | Activity Myc/Max | Cytotox (cancer) | Cytotox (control) |
|---|---|---|---|---|---|
| CG-RS-123 | 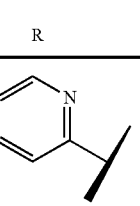 | 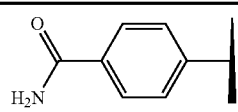 | – | – | – |
| CG-RS-125 | 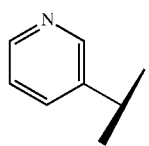 | 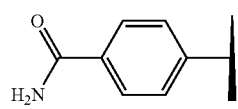 | | | |

-continued
| | | | | | |
|---|---|---|---|---|---|
| CG-RS-128 | 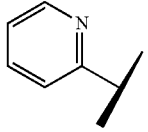 | 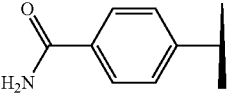 | − | − | − |
| CG-RS-129 | 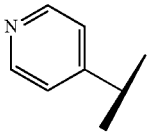 | 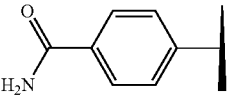 | +++ | − | −/+ |
| CG-RS-130 | 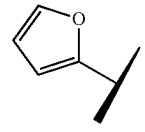 | 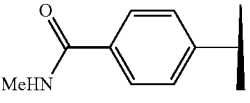 | | | |
| CG-RS-131 | 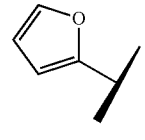 | 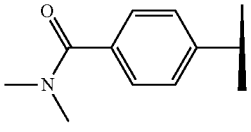 | | − | + |
| CG-RS-134 | 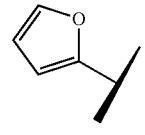 | 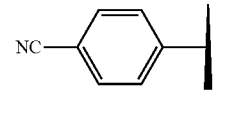 | | − | +++ |
| CG-RS-136 | 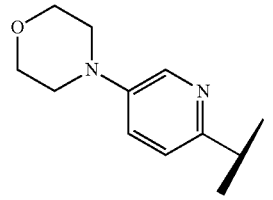 | 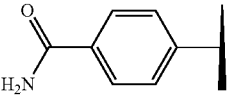 | | − | − |
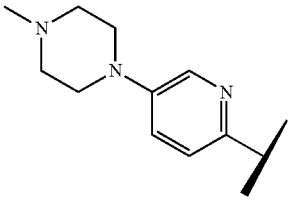
| | | | | | |
|---|---|---|---|---|---|
| CG-RS-137 | 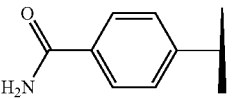 | 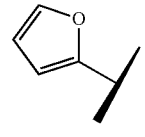 | | +++ | +++ |
| CG-RS-143 | 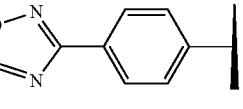 | 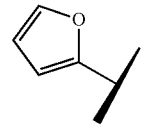 | | − | − |
| CG-RS-147 | | 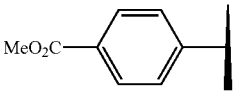 | | − | +++ |

| | | | Activity Myc/Max | Cytotox (cancer) | Cytotox (control) |
|---|---|---|---|---|---|
| CG-RS-148 | 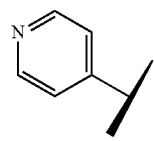 | 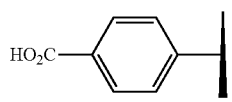 | | − | + |
| CG-RS-109B | 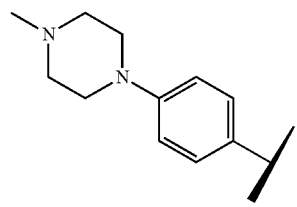 | 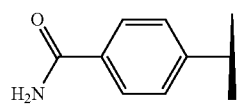 | | − | +++ | − |
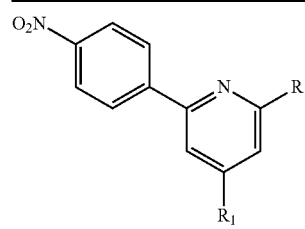
| | R | Activity Myc/Max | Cytotox (cancer) | Cytotox (control) |
|---|---|---|---|---|
| SJ2-68 | 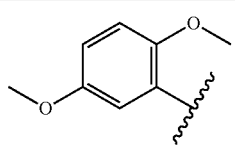 | | | |
| SJ2-70 | 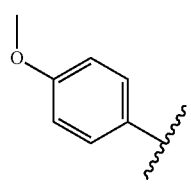 [SMILES: *c1ccc(OC)cc1] | | − | − |
| SJ2-72 | 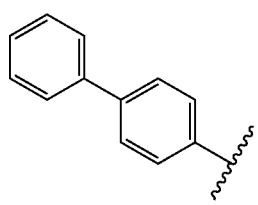 [SMILES: *c1ccc(-c2ccccc2)cc1] | | − | − |
| SJ2-73 | 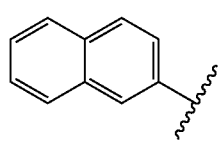 [SMILES: *c1ccc2ccccc2c1] | | − | − |
| KDJ-9 | 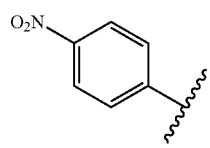 [SMILES: *c1ccc([N+](=O)[O-])cc1] | | + | +++ |

-continued
| | | | |
|---|---|---|---|
| KDJ-1 | 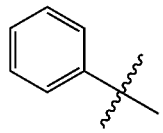 [SMILES: *c1ccccc1] | −/+ | + |
| SJ2-82 | 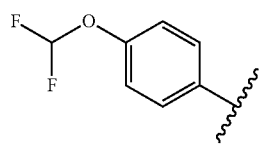 [SMILES: *c1ccc(OC(F)F)cc1] | + | − |
| | 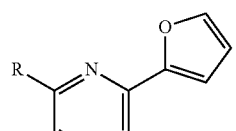 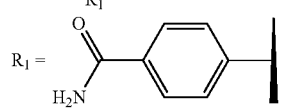 | | |
| SJ2-83 | 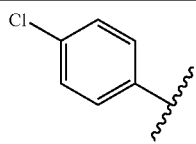 | − | − |
| SJ2-84 | 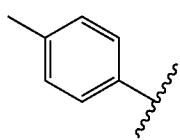 [SMILES: *c1ccc(C)cc1] | + | − |
| SJ2-85 | 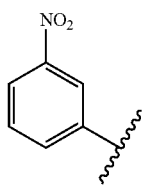 [SMILES: *c1cccc([N+](=O)[O-])c1] | + | − |
| SJ2-115 | 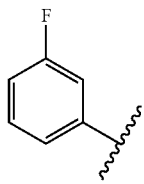 [SMILES: *c1cccc(F)c1] | + | − |
| SJ2-116 | 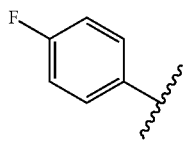 | + | − |
| SJ2-117 | 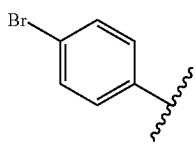 | + | − |

-continued
| | | | |
|---|---|---|---|
| SJ2-119 | 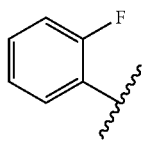 [SMILES: *c1ccccc1F] | + | + |
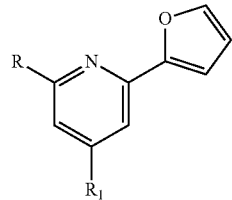
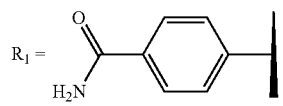
| | | | |
|---|---|---|---|
| SJ2-133 | 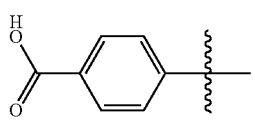 | − | − |
| SJ2-136 | 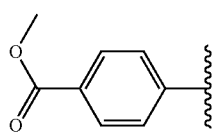 | + | +++ |
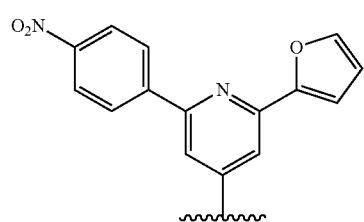 [SMILES: *c1cc(-c2ccc([N+](=O)[O-])cc2)nc(-c2ccco2)c1]
| | |
|---|---|
| HJX-I-11 | 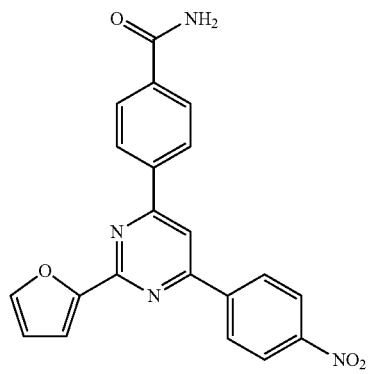 [SMILES: NC(=O)c1ccc(-c2cc(-c3ccc([N+](=O)[O-])cc3)nc(-c3ccco3)n2)cc1] |
HJX-I-11

HJX-I-13

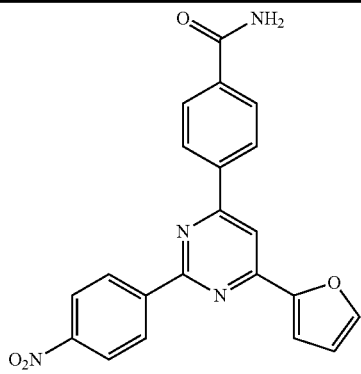

HJX-I-13

It should be noted that CG-RS-44 is also called KDJ-Pyr-9, and CG-RS-50 is also called KDJ-Pyr-10.

As evidenced by the above described compounds, the invention provides a new series of small molecule antagonists of the MYC-MAX PPI. The most potent members of this family of compounds can bind to both Myc and MYC-MAX with nanomolar affinity. These compounds also inhibit MYC-driven oncogenic transformation as well as Myc-dependent transcriptional regulation. They showed a strong effect on the viability and proliferative capacity of several human cancer cells lines. These effects are particularly striking in the case of leukemia cells, but they extend to cell lines derived from solid tumors as well. The promising pharmacokinetic properties of these molecules also allowed further in vivo studies. It was found that these inhibitors of the MYC-MAX PPI can effectively interfere with the growth of a Myc-driven xenograft tumor and block tumor growth.

Procedures for preparation of some analog compounds on solid support are shown below.

Scheme 1. Preparation of compounds on Rink amide solid support

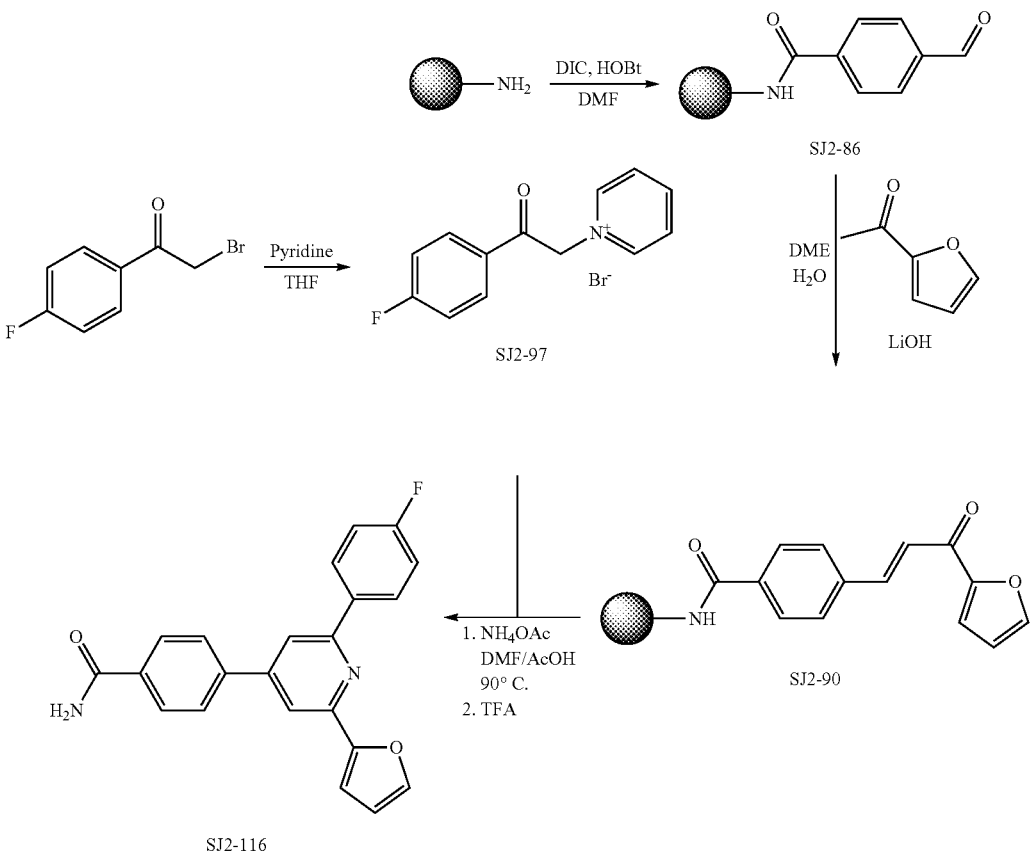

Immobilization of Compounds on Solid Support SJ2-86

4-Carboxybenzaldehyde (0.72 g, 4.8 mmol, 3.0 eq), hydroxybenzotriazole (HOBt) (0.74 g, 4.8 mmol, 3.0 eq.) and N,N'-diisopropylcarbodiimide (DIC) (0.76 mL, 0.61 g, 4.8 mL, 3.0 eq.) were added to a suspension of deprotected Rink amide resin (2.2 g, 0.73 mmol/g, 1.6 mmol) in N,N-dimethylformamide (DMF) (8.0 mL). After 12 h of vigorous shaking, the solvent was removed by filtration under suction and the resin was successively washed with DMF, MeOH, and $CH_2Cl_2$ (3×3×10 mL). The quantitative acylation of the amine on the resin was confirmed by a negative free-amine TNBS test.

Compound SJ2-90

Benzaldehyde functionalized resin SJ2-86 (1.0 g, 0.66 mmol/g, 0.66 mmol) was suspended in a mixture of 2-acetylfuran (0.17 g, 1.5 mmol, 2.0 eq) and powdered LiOH (36 mg, 1.5 mmol, 2.0 eq) in dimethoxyethane (DME) (9.8 mL) and H2O (0.20 mL). After 36 h of vigorous shaking, the solvent was removed by filtration under suction and the resin was successively washed with acetic acid, DMF, MeOH, and $CH_2Cl_2$ (4×3×10 mL). The completion of the reaction was confirmed by LC-MS analysis of a small sample of the resin cleaved using trifluoroacetic acid (TFA) for 1 h. Incomplete reactions were repeated. Due to its strong intrinsic fluorescence, compound SJ2-90 exhibits a characteristic negative absorbance signal at 214 nm in the UV-Vis chromatogram.

Phenacylpyridinium bromides were obtained using the method illustrated by the following synthesis of compound SJ2-97.

Compound SJ2-97

Pyridine (80 uL, 1.0 mmol, 2.0 eq.) was added a solution of 2-bromo-4'-fluoroacetophenone (0.11 g, 0.50 mmol) in dry tetrahydrofuran (2.0 mL) under vigorous stirring. The formation of a colorless precipitate became visible after ~20 min and the stirring was continued for 20 h. The precipitate was isolated by filtration, washing with a minimal amount of cold diethylether and drying under vacuum to yield SJ2-97 as a colorless crystalline solid (0.147 g, quant.).

Compound SJ2-116

Phenacylpyridinium SJ2-97 (89 mg, 0.30 mmol) was added to a suspension of resin SJ2-90 resin (0.17 g, 0.10 mmol) in DMF (2.0 mL), acetic acid (1.3 mL) and $NH_4OAc$ (0.23 g, 3.0 mmol, 30 eq.). The suspension was stirred at 90° C. for 60 h. The resin was washed successively with DMF, MeOH, and $CH_2Cl_2$ (3×3×5 mL). The product was cleaved from the resin with TFA (4.0 mL) for 2 h, evaporated to dryness under vacuum and purified by preparative TLC on silica. Rf=($CH_2Cl_2$/MeOH, 93:7) 0.55, to yield SJ2-116 (4.59 mg, 12.8%) as a pale yellow solid whose purity and identity was further confirmed by LC-MS.

Different analogues for structure-activity relationship studies are prepared using the procedures described above.

Procedures for Preparation of Compounds in Solution
Scheme 2. Solution Phase Synthesis of KDJ-9 and Analogues Compound SJ2-123

2-Acetylfuran (55 mg, 0.50 mmol) and LiOH (12 mg, 0.50 mmol) were stirred in MeOH (2.5 mL) for 1 h before methyl 4-formylbenzoate (82 mg, 0.50 mmol) was added. After ~45 min a thick colorless precipitate was formed and the suspension was vigorously stirred for an additional 1 h 45 min. The precipitate was then separated by centrifugation, acetic acid (3%, 3.0 mL) was added to the supernatant and additional precipitate was isolated by further centrifugation. The combined solids were dried under vacuum to yield SJ2-123 as a colorless solid (88.5 mg, 69.1%).

Compound SJ2-136

The chalcone SJ2-123 (0.60 g, 2.4 mmol), the phenacylpyridinium bromide SJ2-127 (0.76 g, 2.4 mmol) and $NH_4OAc$ (5.4 g, 71 mmol, 30 eq) were stirred in a mixture of acetic acid (24 mL) and DMF (36 mL). at 90° C. for 24 h. $NaHCO_3$ sat. (20 mL) was added followed by powdered $NaHCO_3$ by portions until the gas release ceased. The mixture was dried in vacuum and the residue washed with $CH_2Cl_2$/acetone (1:1) until colorless. The solution was evaporated in vacuum and the resulting solid purified by silica gel chromatography (8.0×4.5 cm) using pure $CH_2Cl_2$, Rf=0.57, as eluent to yield SJ2-136 (0.463 g, 48.2%) as a pale yellow solid.

Compound SJ2-140

LiOH (96 mg, 4.0 mmol) in $H_2O$ (5.0 mL) was added to a solution of SJ2-136 (0.40 g, 1.0 mmol) in THF (45 mL) and stirred for 72 h. The solvent was evaporated and the residue purified by flash chromatography on silica gel (6.5× 4.5 cm) using $CH_2Cl_2$/MeOH (95:5) as eluent Rf($CH_2Cl_2$/ MeOH, 95:5)=0.26 to yield SJ2-140 as a pale yellow solid (0.38 g, 98.4%).

Compound KDJ-9

Oxalyl chloride (0.39 mL, 0.57 g, 4.5 mmol, 5.0 eq) was added to a solution SJ2-140 (0.35 g, 0.90 mmol) in $CH_2Cl_2$ (27 mL) and DMF (0.13 mL) and stirred for 20 h. Concentrated $NH_3$ (20 mL) was added and the mixture stirred vigorously for 30 min. The organic phase was evaporated by rotatory evaporation and the resulting precipitate was isolated from the aqueous phase by filtration. The vacuum dried residue was purified by flash chromatography on silica gel (5×4.5 cm) using MeOH/$CH_2Cl_2$ (3.0→5.0%) as eluent. Rf($CH_2Cl_2$/MeOH, 95:5)=0.34 to yield KDJ-9 (0.34 g, 97.9%) as a pale yellow solid.

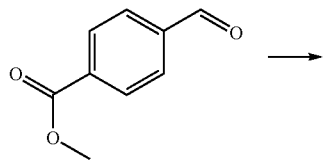

33

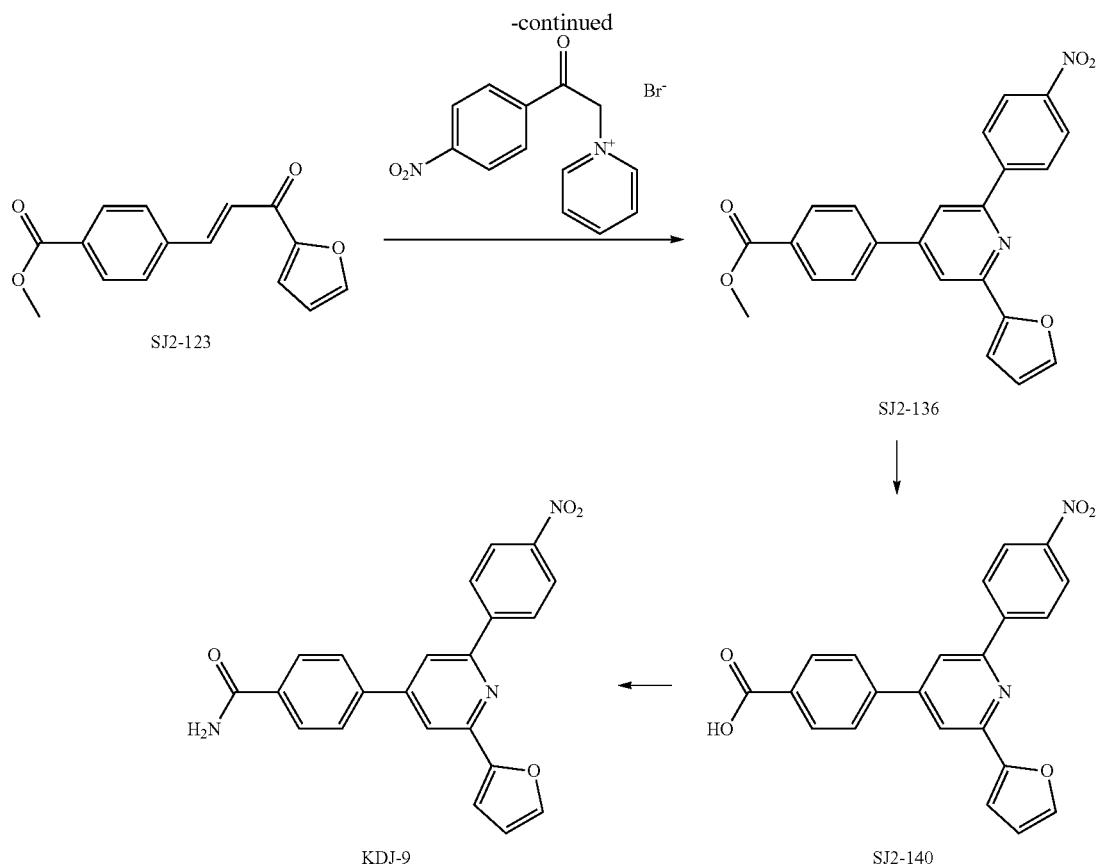

34

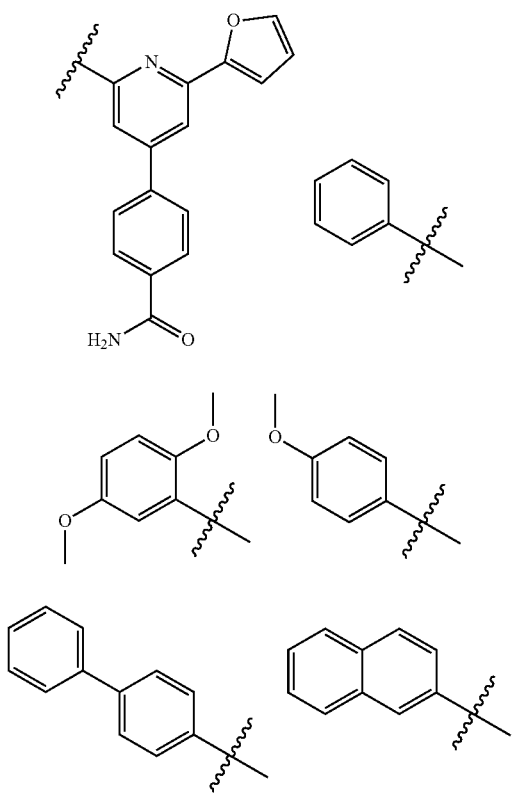

IV. Therapeutic Applications

The c-Myc inhibitor compounds described herein can be useful in various therapeutic or prophylactic (e.g., antitumor) applications. They can be readily employed for suppressing or inhibiting c-Myc mediated cellular activities, and treating cancers or preventing the development of tumors (esp. Myc-dependent tumors). Accordingly, the invention provides methods for inhibiting c-Myc mediated biochemical activities or c-Myc signaling pathway in a cell (e.g., tumor cell). In some embodiments, the cell is present in a subject (e.g., a subject afflicted with cancer). In some embodiments, the therapeutic applications of the invention are directed to preventing development of tumor or treating cancer in a subject. Typically, the therapeutic methods of the invention entail administering to a subject a pharmaceutical composition that comprises an effective amount of a c-Myc-inhibiting agent described herein (e.g., KJ-Pyr-9 or a derivative thereof). Novel c-Myc inhibitors that can be identified in accordance with the screening methods of the invention can also be employed.

In another aspect, the invention provides methods for inhibiting c-Myc signaling pathway in a cell. The methods involve contacting the cell with an effective amount of a compound disclosed herein, e.g., a compound selected from the group consisting of 4-(2-(furan-2-yl)-6-(4-nitrophenyl) pyridin-4-yl)benzamide (KJ-Pyr-9), 5-(2-(furan-2-yl)-6-(4-nitrophenyl)pyridin-4-yl)furan-2-carboxamide (KJ-Pyr-10), 5-(2-(furan-2-yl)-6-(4-methoxyphenyl)pyridin-4-yl)furan-2-carboxamide (KJ-Pyr-6), and 4'-(2-(furan-2-yl)-6-phenylpyridin-4-yl)-[1,1'-biphenyl]-4-carboxamide (KJ-Pyr-4), a derivative or analog thereof (e.g., an analog compound as exemplified herein), and a pharmaceutically acceptable salt thereof. In some methods of the invention, the employed compound is 4-(2-(furan-2-yl)-6-(4-nitrophenyl)pyridin-4-yl)benzamide (KJ-Pyr-9) or 5-(2-(furan-2-yl)-6-(4-nitrophenyl)pyridin-4-yl)furan-2-carboxamide (KJ-Pyr-10). In some other methods, the employed compound is a derivative or variant of the parent compound, KJ-Pyr-9, KJ-Pyr-10, KJ-Pyr-6, or KJ-Pyr-4. In these derivative or variant compounds, one or more mono- or multi-valent groups of the parent compound are substituted with a different mono- or multi-valent group. The substituting group can be independently selected from the group consisting of: H; halogen; straight, cyclic or branched chain alkyl; straight, cyclic or branched chain alkenyl; straight, cyclic or branched chain alkynyl; halo-alkyl, -alkenyl or -alkynyl; CN; $CF_3$; aryl and substituted aryl groups in which any or all H groups of the aryl ring is substituted with a different group; heterocyclic and substituted heterocyclic groups in which any or all groups of the aryl ring is substituted with a different group; carboxyl; carbonyl, alkoxyl; alkyloxyalkanes; alkoxycarbonyl; aryloxyl, heterocyclyloxyl; hydroxyl; amine; amide; amino; quaternary amino; nitro; sulfonyl; alkylamine; silyl, siloxyl; saturated C—C bonds; unsaturated C—C bonds; ester, ether, amino; amide, urethane, carbonyl, acetyl and ketyl groups; hetero atoms N, S and O; polymer groups; and amino acids. In some of the methods, one or more hydrogens of the parent compound are substituted with a lower alkyl group.

Some methods of the invention are directed to inhibiting c-Myc signaling pathway in a tumor cell. For example, the methods can be used for inhibiting c-Myc signaling pathway in a cell of colon cancer, breast cancer, cervical cancer, a small cell lung carcinoma, an osteosarcoma, a glioblastoma, melanoma, or a myeloid leukemia. In some of these methods, the tumor cell is present in vivo in a subject. The compound can be administered to the subject in a pharmaceutical composition as described herein.

In a related aspect, the invention provides methods of inhibiting growth or proliferation of a cell in a subject. These methods entail administering to the subject an effective amount of a compound that inhibits c-Myc signaling activities. The administered compound is selected from the group consisting of 4-(2-(furan-2-yl)-6-(4-nitrophenyl)pyridin-4-yl)benzamide (KJ-Pyr-9), 5-(2-(furan-2-yl)-6-(4-nitrophenyl)pyridin-4-yl)furan-2-carboxamide (KJ-Pyr-10), 5-(2-(furan-2-yl)-6-(4-methoxyphenyl)pyridin-4-yl)furan-2-carboxamide (KJ-Pyr-6), and 4'-(2-(furan-2-yl)-6-phenylpyridin-4-yl)-[1,1'-biphenyl]-4-carboxamide (KJ-Pyr-4), a derivative or analog thereof (e.g., an analog compound as exemplified herein), and a pharmaceutically acceptable salt thereof.

In some of the methods, the administered compound is 4-(2-(furan-2-yl)-6-(4-nitrophenyl)pyridin-4-yl)benzamide (KJ-Pyr-9) or 5-(2-(furan-2-yl)-6-(4-nitrophenyl)pyridin-4-yl)furan-2-carboxamide (KJ-Pyr-10). In some other methods, the administered compound is a derivative or variant of the parent compound, KJ-Pyr-9, KJ-Pyr-10, KJ-Pyr-6, or KJ-Pyr-4. In the derivative or variant compound, one or more mono- or multi-valent groups of the parent compound are substituted with a different mono- or multi-valent group. The substituting group can be independently selected from the group consisting of: H; halogen; straight, cyclic or branched chain alkyl; straight, cyclic or branched chain alkenyl; straight, cyclic or branched chain alkynyl; halo-alkyl, -alkenyl or -alkynyl; CN; $CF_3$; aryl and substituted aryl groups in which any or all H groups of the aryl ring is substituted with a different group; heterocyclic and substituted heterocyclic groups in which any or all groups of the aryl ring is substituted with a different group; carboxyl; carbonyl, alkoxyl; alkyloxyalkanes; alkoxycarbonyl; aryloxyl, heterocyclyloxyl; hydroxyl; amine; amide; amino; quaternary amino; nitro; sulfonyl; alkylamine; silyl, siloxyl; saturated C—C bonds; unsaturated C—C bonds; ester, ether, amino; amide, urethane, carbonyl, acetyl and ketyl groups; hetero atoms N, S and O; polymer groups; and amino acids. In some methods, one or more hydrogens of the parent compound are substituted with a lower alkyl group.

Some of the methods are directed to inhibiting growth or proliferation of a tumor cell in a subject. For example, the methods can be used for inhibiting growth of a cell of colon cancer, breast cancer, cervical cancer, a small, cell lung carcinoma, an osteosarcoma, a glioblastoma, melanoma, or a myeloid leukemia.

In another related aspect, the invention provides methods for treating cancer or preventing the development of a tumor in a subject. These methods entail administering to the subject a therapeutically effective amount of a compound that inhibits c-Myc signaling pathway. The compound is selected from the group consisting of 4-(2-(furan-2-yl)-6-(4-nitrophenyl)pyridin-4-yl)benzamide (KJ-Pyr-9), 5-(2-(furan-2-yl)-6-(4-nitrophenyl)pyridin-4-yl)furan-2-carboxamide (KJ-Pyr-10), 5-(2-(furan-2-yl)-6-(4-methoxyphenyl) pyridin-4-yl)furan-2-carboxamide (KJ-Pyr-6), and 4'-(2-(furan-2-yl)-6-phenylpyridin-4-yl)-[1,1'-biphenyl]-4-carboxamide (KJ-Pyr-4), a derivative or analog thereof (e.g., an analog compound as exemplified herein), and a pharmaceutically acceptable salt thereof. In some of these methods, the employed compound is 4-(2-(furan-2-yl)-6-(4-nitrophenyl)pyridin-4-yl)benzamide (KJ-Pyr-9) or 5-(2-(furan-2-yl)-6-(4-nitrophenyl)pyridin-4-yl)furan-2-carboxamide (KJ-Pyr-10). In some other methods, an analog, derivative, or variant of the KJ-Pyr-9, KJ-Pyr-10, KJ-Pyr-6, or KJ-Pyr-4 compound is used. Some of the methods are directed to treating subjects afflicted with a tumor selected from the group consisting of colon cancer, breast cancer, cervical cancer, small cell lung carcinomas, osteosarcomas, glioblastomas, melanoma and myeloid leukemias.

The cancers and tumors suitable for treatment with compositions and methods of the present invention can be those present in a variety of tissues and organs. They also include cancer cells, tumor cells, which include malignant tumor cells, and the like that are found in the component cells of these tissues and/or organs. Examples include brain tumors (glioblastoma multiforme and the like), spinal tumors, maxillary sinus cancer, cancer of the pancreatic gland, gum cancer, tongue cancer, lip cancer, nasopharyngeal cancer, mesopharyngeal cancer, hypopharyngeal cancer, laryngeal cancer, thyroid cancer, parathyroid cancer, lung cancer, pleural tumors, cancerous peritonitis, cancerous pleuritis, esophageal cancer, stomach cancer, colon cancer, bile duct cancer, gallbladder cancer, pancreatic cancer, hepatic cancer, kidney cancer, bladder cancer, prostate cancer, penile cancer, testicular tumors, cancer of the adrenal glands, uterocervical cancer, endometrial cancer, vaginal cancer, vulvar cancer, ovarian cancer, ciliated epithelial cancer, malignant bone tumors, soft-tissue sarcomas, breast cancer, skin cancer, malignant melanomas, basal cell tumors, leukemia, myelofibrosis with myeloid metaplasia, malignant lymphoma tumors, Hodgkin's disease, plasmacytomas, and gliomas.

Generally, the treatment should affect a subject, tissue or cell to obtain a desired pharmacologic and/or physiologic effect. The effect may be prophylactic in terms of completely or partially preventing a disease or sign or symptom thereof. It can also be therapeutic in terms of a partial or complete cure for a disease or disorder (e.g., tumor growth) that is associated with or mediated by abnormal c-Myc expression or biochemical activities, or amelioration of adverse effect that is attributable to the disorder. Suitable subjects include an invertebrate, a vertebrate, a mammal, particularly a human. The c-Myc inhibitor compounds described in the present invention can be used alone or in conjunction with any of various drugs, including known antitumor drugs (antineoplastic drugs), tumor metastasis-inhibitors, inhibitors for thrombogenesis, therapeutic drugs for joint destruction, analgesics, anti-inflammatory drugs, immunoregulators (or immunomodulators) and/or immunosuppressants, which can be employed as not being restricted to particular species as long as they serve effectively or advantageously.

The compounds can be administered alone to a subject in need of treatment. More preferably, they are administered in the form of a pharmaceutical composition or preparation in admixture with any of various pharmacologically-acceptable additives. For example, the compounds may be administered in the form of a convenient pharmaceutical composition or formulation suitable for oral, topical, parenteral application, or the like. Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for molecules of the invention include ethylene-vinyl acetate copolymer particles, osmotic pumps, implantable infusion systems, and liposomes. Formulations for inhalation may contain excipients, for example, lactose, or may be aqueous solutions containing, e.g., polyoxyethylene-9-lauryl ether, glycocholate and deoxycholate, or may be oily solutions for administration in the form of nasal drops, or as a gel.

Pharmaceutical composition containing a c-Myc-inhibiting compound can be administered locally or systemically in a therapeutically effective amount or dose. They can be administered parenterally, enterically, by injection, rapid infusion, nasopharyngeal absorption, dermal absorption, rectally and orally. The c-Myc inhibitors for use in the methods of the invention should be administered to a subject in an amount that is sufficient to achieve the desired therapeutic effect (e.g., eliminating or ameliorating symptoms associated with tumor development and growth) in a subject in need thereof. Typically, a therapeutically effective amount or efficacious dose of the c-Myc inhibitor employed in the pharmaceutical compositions of the invention should inhibit c-Myc signaling activities in a cell, or slow or suppress tumor growth in a subject. As noted below, actual dosage levels of the active ingredients in the pharmaceutical compositions of the present invention can be varied so as to obtain an amount of the active ingredient which is effective to achieve the desired therapeutic response without being toxic to the subject.

The selected dosage level depends upon a variety of pharmacokinetic factors including the activity of the particular compositions of the present invention employed, the route of administration, the time of administration, and the rate of excretion of the particular compound being employed. It also depends on the duration of the treatment, other drugs, compounds and/or materials used in combination with the particular compositions employed, the age, gender, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. For a given c-Myc-inhibitor compound, one skilled in the art can easily identify the effective amount of an agent that inhibits c-Myc by using routinely practiced pharmaceutical methods. Dosages used in vitro or in situ studies may provide useful guidance in the amounts useful for in vivo administration of the pharmaceutical composition, and animal models may be used to determine effective dosages for treatment of particular disorders. Typically, a pharmaceutically effective dosage would be between about 0.001 and 100 mg/kg body weight of the subject to be treated.

The c-Myc inhibitor compounds and other therapeutic regimens described herein are usually administered to the subjects on multiple occasions. Intervals between single dosages can be daily, weekly, monthly or yearly. Intervals can also be irregular as indicated by measuring blood levels of the c-Myc inhibitor compounds and the other therapeutic agents used in the subject. In some methods, dosage is adjusted to achieve a plasma compound concentration of 1-1000 μg/ml, and in some methods 25-300 μg/ml or 10-100 μg/ml. Alternatively, the therapeutic agents can be administered as a sustained release formulation, in which case less frequent administration is required. Dosage and frequency vary depending on the half-life of the c-Myc inhibitor compound and the other drugs in the subject. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

General procedure for the synthesis of phenacyl pyridinium salts: 4'-Nitro-2-bromoacetophenone (4.9 g, 20 mmol) was taken in THF (80 mL) at room temperature under nitrogen. Pyridine (6.4 mL, 80 mmol) was added dropwise. The resulting turbid solution was stirred for ~6 h, filtered. The filter cake was washed with ether (40 mL×3), dried under vacuum to afford 6.0 g of the pyridinium salt. Similar procedure was followed for the preparation of CG-RS-46 (2.6 g), CG-RS-52 (1.2 g), CG-RS-53 (1.2 g), CG-RS-56 (1.0 g), CG-RS-57 (1.0 g), CG-RS-60 (690 mg), CG-RS-63 (1.05 g), CG-RS-65 (286 mg), CG-RS-69 (400 mg), CG-RS-71 (570 mg), CG-RS-80 (2.6 g), and CG-RS-81 (2.4 g), Generalized Scheme for the synthesis of phenacyl pyridinium salts.

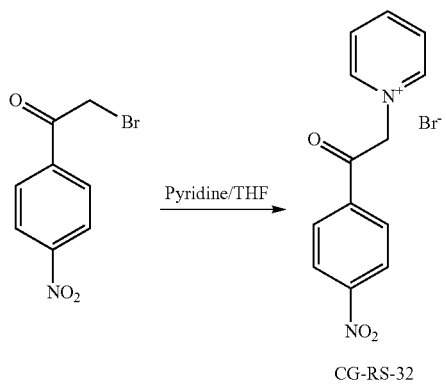 [SMILES: O=C(CBr)c1ccc([N+](=O)[O-])cc1 ; O=C(C[n+]1ccccc1)c1ccc([N+](=O)[O-])cc1 ; [Br-]]

CG-RS-32

EXAMPLES

The following examples are offered to illustrate, but not to limit the present invention.

Example 1. Identification and Biochemical Activities of Novel Myc Inhibitors

Screening: Effective inhibitors of Myc were identified by screening a Krohnke pyridine library of small molecule compounds (Fujimori et al., J. Combinatorial Chem. 5:625-631, 2003) with fluorescence polarization for inhibition of MYC-MAX dimerization. The human MYC and MAX bHLH-LZ domains were expressed in E. coli and combined with an E-box DNA duplex labeled with Alexa Fluor 594. When these 3 components are mixed, MYC and MAX heterodimerize and bind to the E-box DNA. This binding results in an increase in the fluorescence polarization of the Alexa Fluor 594 signal. Compounds that inhibit the formation of this complex cause a decrease in the fluorescence polarization, and this activity was used in a screen for inhibitors of MYC-MAX dimerization. Initial library screening was conducted with mixtures. Those mixtures that showed the strongest inhibition were resynthesized as individual compounds and rescreened, yielding four effective molecules shown in FIG. 1. The relative binding affinities of each of these compounds for MYC-MAX and MAX-MAX were reassessed, vide supra, and the four selected structures displayed significantly higher affinity for MYC-MAX over MAX-MAX dimers.

Specificity of inhibition: An assay of Myc-induced oncogenic transformation in chicken embryo fibroblasts (CEF) was used as a secondary screen to determine inhibition of Myc in a biological setting. CEF were infected with the retroviral expression vector RCAS, mediating expression of ATG-Myc, a variant of human Myc that has the non-canonical CTG start codon replaced by an ATG start codon. The ATG start codon mediates higher expression and greater potency in oncogenic transformation resulting in the formation of focal microtumors in the cell monolayer. In this secondary screen, only KJ-Pyr-9 and KJ-Pyr-10 were effective in countering the oncogenic activity of Myc (Table 1). We surmise that failure to show a cellular effect is likely the result of poor compound solubility in culture media. As KJ-Pyr-9 had the best aqueous solubility of the four compounds selected, all further experiments were conducted with KJ-Pyr-9.

TABLE 1

Effects of inhibitor compounds on the efficiency of Myc-induced oncogenic transformation.

| Compound | EOT[1] |
|---|---|
| KJ-Pyr-4 | 1.12 |
| KJ-Pyr-6 | 0.79 |
| KJ-Pyr-9 | 0.00083 |
| KJ-Pyr-10 | 0.00017 |

Figure 2:
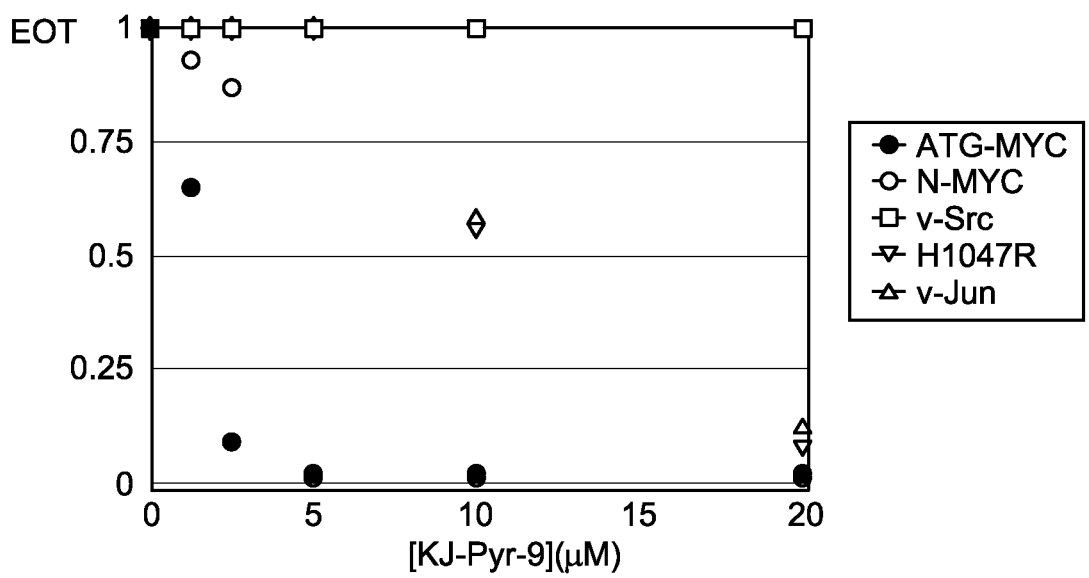
FIG. 2 shows dose response of KJ-Pyr-9 versus oncogenic transformation induced by MYC, N-MYC, v-Src, PI3K H1047R, and v-Jun. Data from a representative experiment conducted with the cells derived from a single chicken embryo.

[1]EOT (efficiency of transformation) = focus counts in the presence of inhibitor over focus counts of control plates The assay of oncogene-induced cellular transformation in CEF was also used to determine selectivity of KJ-Pyr-9 for Myc. KJ-Pyr-9 was tested against ATG-Myc, N-Myc and three unrelated oncoproteins, v-Src, v-Jun and the H1047R mutant of phosphatidylinositol 3-kinase (FIG. 2). The oncogenic activity of N-Myc and ATG-Myc was strongly inhibited by KJ-Pyr-9, whereas the unrelated oncoproteins were either unaffected (v-Src) or were inhibited at significantly higher concentrations (v-Jun, PI3K H1047R).

Binding of KJ-Pyr-9 to 10. vc: KJ-Pyr-9 has a low solubility in water (12.5 µM). Because of this limitation, many commonly used methods such as analytical ultracentrifugation, isothermal calorimetry and non-covalent mass spectrometry fail to provide definitive evidence for direct binding. However, we were able to demonstrate a direct interaction and determine a binding constant for KJ-Pyr-9 and Myc using backscattering interferometry (BSI) (Baksh et al., Nat. Biotech. 29:357-360, 2011). The results shown in Table 2 indicate that KJ-Pyr-9 directly binds to Myc (6.5 nM) as well as to the MYC-MAX heterodimer (13.4 nM) but only weakly to the MAX homodimer (>1 uM). The data suggest that KJ-Pyr-9 is capable of binding to the disordered monomeric form of MYC and that it can dissociate the intact MYC-MAX complex. In contrast, another member of the same library, KJ-Pyr-1, which lacks the nitro substituent and has no Myc-inhibitory activity, binds much more weakly (230 nM) to Myc. This compound was also tested in a transformation assay and found to be ineffective as an inhibitor of Myc.

TABLE 2

Dissociation constants of KJ-Pyr-9 and MYC, MAX and the MYC-MAX dimer as measured by backscattering interferometry (BSI).

| Protein | $K_d$ |
|---|---|
| MYC | 6.5 ± 1.0 nM |
| MYC-MAX | 13.4 ± 3.9 nM |
| MAX | >1.0 μM |

In order to test the ability of KJ-Pyr-9 to enter cells and specifically interfere with the formation of a functional MYC-MAX complex, we applied a protein fragment complementation assay (PCA) based on Renilla Luciferase (Rluc). Rluc-based PCA sentinels have been designed and used to study the dynamics of PPI in vivo (Bachmann et al., *Proc. Natl. Acad. Sci. USA*, 110:8531-8536, 2013; and Stefan et al., *Proc. Natl. Acad. Sci. USA* 104:16916-16921, 2007). An advantage of this assay is that it reports absolute values of protein complex formation in real time. We used an efficient and sensitive PCA biosensor which is based on the PPI involving the full length MAX protein and the C-terminal MAX-interaction-domain in MYC ($MYC^{332-439}$). The assay showed that KJ-Pyr-9 selectively reduced complex formation of $MYC^{332-439}$ with MAX, compared to the effect on an unrelated biosensor based on the homodimer of the protein kinase A (PKA) regulatory subunits (RII:RII) used here as a control. KJ-Pyr-9 also interfered with MAX homodimerization, albeit to a lesser degree than MYC-MAX heterodimerization. These data suggest that the inhibitor compounds disclosed herein enter cells and specifically interfere with MYC-MAX complex formation.

Example 2. Myc Inhibitors Antagonize Myc Mediated Cellular Activities

Figure 3A:
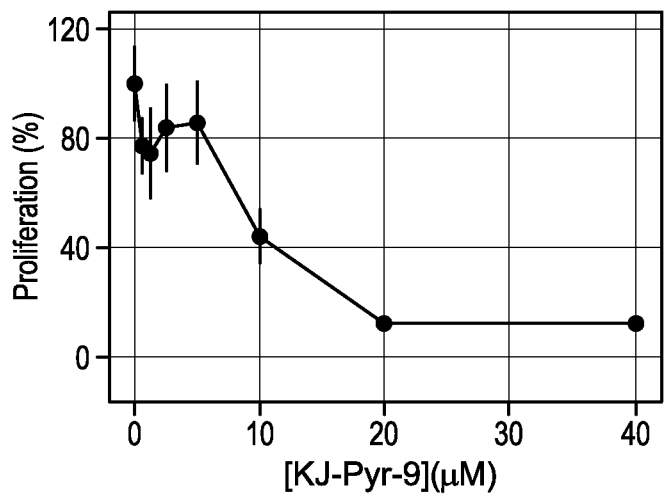
FIGS. 3A-3C show effect of KJ-Pyr-9 on cell proliferation. Dose response curves of the effect of KJ-Pyr-9 on the proliferation of (A) NCI-H460 (ATCC), (B) MDA-MB-231 (NCI), and (C) SUM-159PT (Asterand).
Figure 3B:
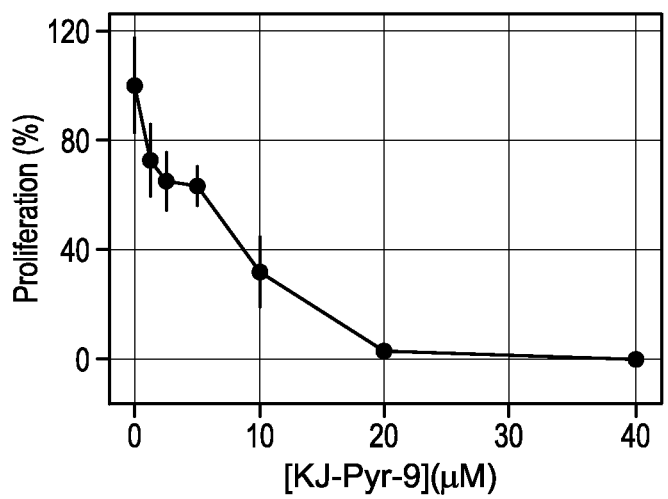
Figure 3C:
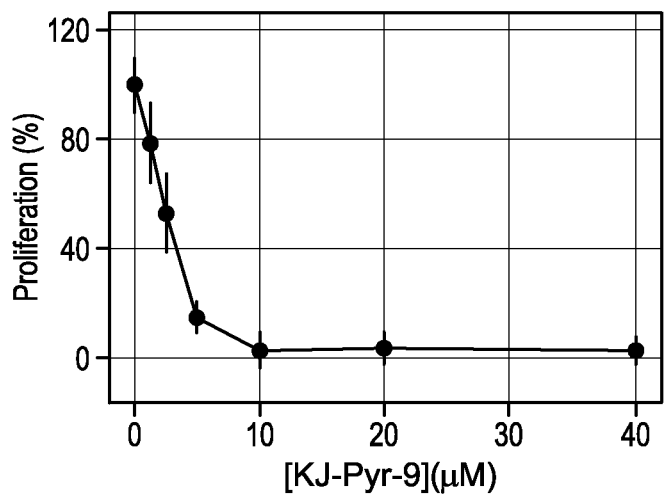
Figure 6A:
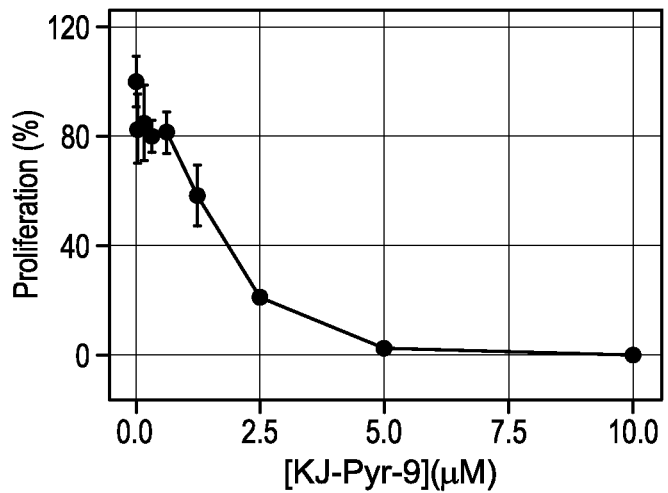
FIGS. 6A-6C show that Burkitt lymphoma-derived cell lines are inhibited by KJ-Pyr-9. (A) Akata, (B) Ramos, (C) Raji. $10^3$ cells were seeded per well on 96-well plates and were treated with the indicated concentrations of KJ-Pyr-9 for 72 hours. Cell proliferation was determined by resazurin fluorescence.
Figure 6B:
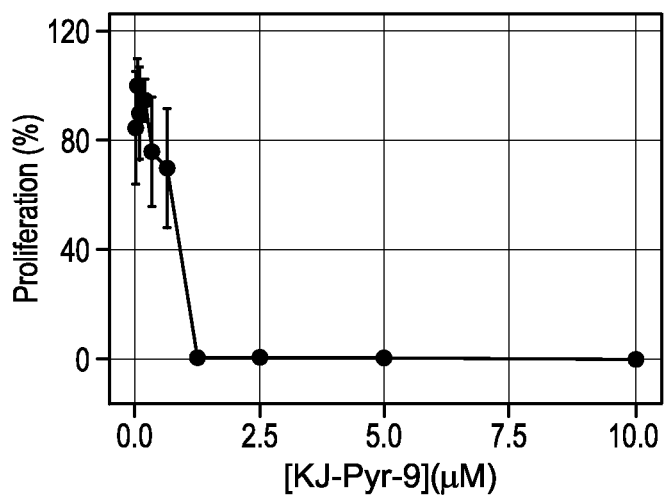
Figure 6C:
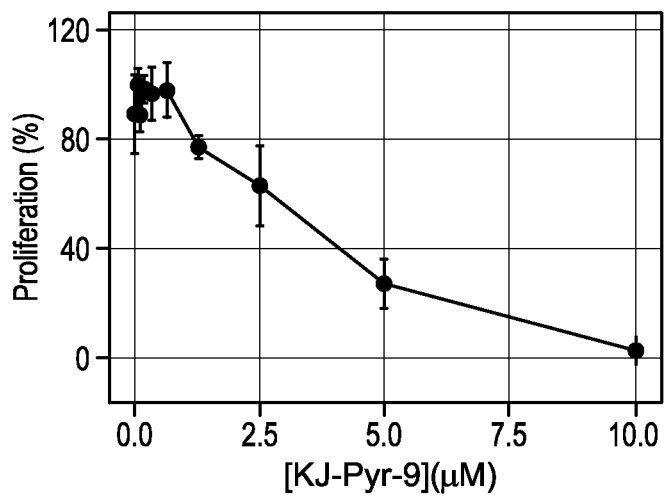
Figures 7A, 7B:
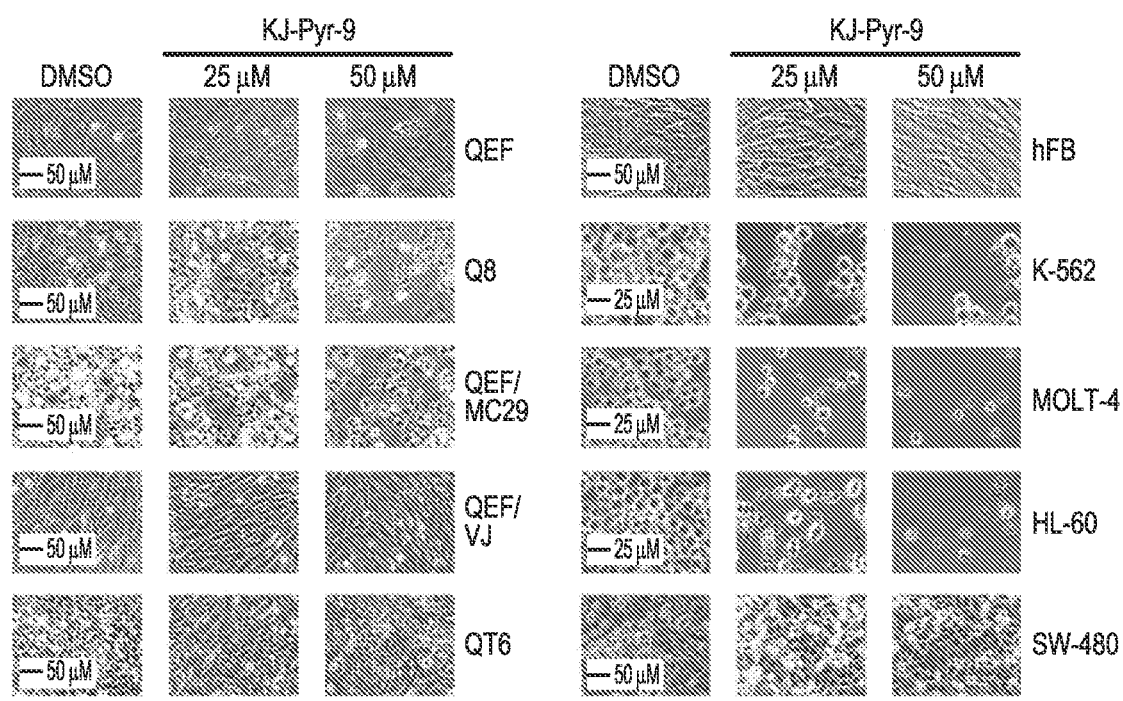
FIGS. 7A-7B show effect of KJ-Pyr-9 on the proliferation of v-myc-transformed quail embryo fibroblasts (A) and of human leukemia and carcinoma cell lines (B). The compound was added in the indicated concentrations to primary quail embryo fibroblasts (QEF), quail cell lines transformed by the oncogenes v-myc (Q8, QEF/MC29), v-jun (VJ), or by methylcholanthrene (QT6), and to human skin fibroblasts (hFB), the non-adherently growing leukemia cell lines K-562, MOLT-4, HL-60, or the adenocarcinoma cell line SW-480. As a control, the compound's solvent dimethyl sulfoxide (DMSO) was added to the cells. Microphotographs were taken 24 hrs after addition of the compound.

Effect on cellular proliferation: Elevated activity of Myc is essential in the proliferation of numerous cancer cell lines. We tested KJ-PYR-9 against three cell lines known to be dependent on increased Myc activity: NCI-H460, MDA-MB-231 and SUM-159PT. The proliferation of all three cell lines was inhibited, albeit at varying concentrations of KJ-Pyr-9 (FIG. 3). Additionally, Burkitt's lymphoma cell lines which show constitutively high expression of c-Myc are very sensitive to KJ-Pyr-9 (FIG. 6). KJ-Pyr-9 was also assessed against selected proliferating avian and human cells (FIG. 7). Whereas normal quail embryo fibroblasts (QEF) and QEF oncogenically transformed by the v-jun oncogene or by the chemical carcinogen methylcholanthrene were only slightly impaired in their growth, cells transformed by v-myc were significantly more affected (FIG. 7A). A similar result was obtained with human fibroblasts and distinct human cancer cell lines. Notably, the leukemia cell lines K-562, MOLT-4, and HL-60, which express high levels of the Myc proto-oncogene, were strongly inhibited in their proliferation, whereas human fibroblasts, or the colon carcinoma cell line SW-480 were not affected (FIG. 7B).

High concentrations of serum in the growth medium lowered the antiproliferative activity of the inhibitor. This effect did not result from binding of the compound to serum proteins, as supplementation of low-serum media with bovine serum albumin did not affect inhibitor activity. Rather, the reduced inhibitor activity is likely caused by growth factors supplied with the serum.

Figure 4:
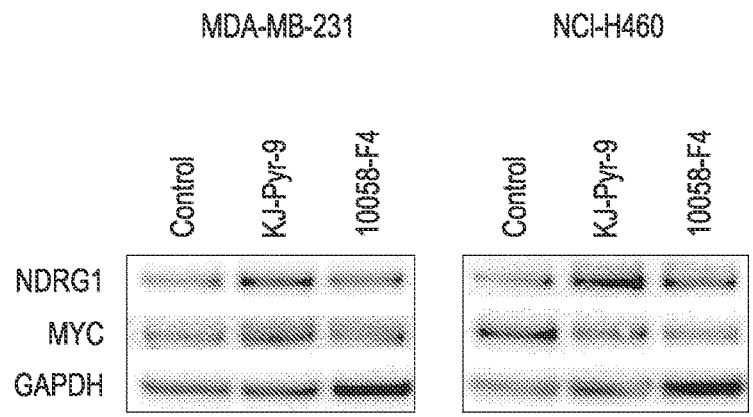
FIG. 4 shows effect of KJ-Pyr-9 on the expression of NDRG in MDA-MB-231 and NCI-H460 cells. NCI-H460 cells were grown in RPMI medium, and MDA-MB-231 cells were grown in DMEM medium; both media contained 10% FBS. KJ-Pyr-9 and 10058-F4 were added at a concentration of 20 µM and the cells were treated for 24 hrs before Western blot analysis.

Interference with Myc transcriptional activity of Myc affects the transcription of a large number of target genes and can function as activator or repressor. We examined the effect of KJ-Pyr-9 on the transcriptional activity of Myc by determining the expression of NDRG1 (N-myc downregulated gene 1) in the presence and absence of Myc inhibition. NDRG1 is a direct transcriptional target of Myc that acts as a repressor of this gene. For comparison, we used the previously identified inhibitor of MYC-MAX dimerization that binds to the disordered monomer and prevents Myc from adopting a conformation needed for the interaction with MAX (Wang et al., *Mol. Cancer Ther.* 6:2399-2408, 2007; and Huang et al., *Exp. Hematol.* 34:1480-1489, 2006). Both KJ-Pyr-9 and 10058-F4 cause an increase of NDRG1 expression (FIG. 4). However, KJ-Pyr-9 has only a slight effect on Myc levels, whereas 10058-F4 causes a strong decrease in the levels of Myc. This observation suggests that the two Myc inhibitors function by different mechanisms.

In vivo activity of KJ-Pyr-9: Previous Myc inhibitors have not been effective in animal model studies. These failures resulted from insufficient affinity toward Myc and poor pharmacokinetic properties. We investigated the pharmacokinetic properties of KJ-Pyr-9 in mouse and rat and found that the concentrations of KJ-Pyr-9 achievable in the blood are sufficient to cause inhibition of c-Myc in vitro (see Example 3). We observed no signs of acute toxicity at a dose of 10 mg/kg. Rather surprisingly, KJ-Pyr-9 crossed the blood brain barrier and was present at higher concentrations in brain tissue than in the blood.

Figure 5A:
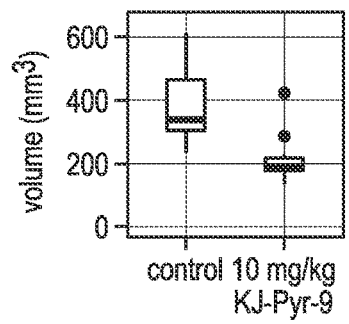
FIGS. 5A-5C show that KJ-Pyr-9 interferes with the growth of a xenograft of MDA-MB-231 cells. Mice were injected with $5\times10^6$ MDA-MB-231 cells subcutaneously into left and right flanks. When tumors reached a volume of 100 mm³ half of the mice were given daily i.p. injections of 10 mg/kg KJ-PYR-9 and the other half received vehicle only. Tumor growth was followed for 31 days. (A) Tumor volumes of treated and untreated animals. (B) Tumor weights of treated and untreated animals. (C) Time course of tumor volumes.
Figure 5B:
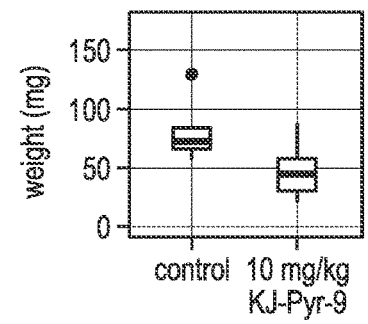
Figure 5C:
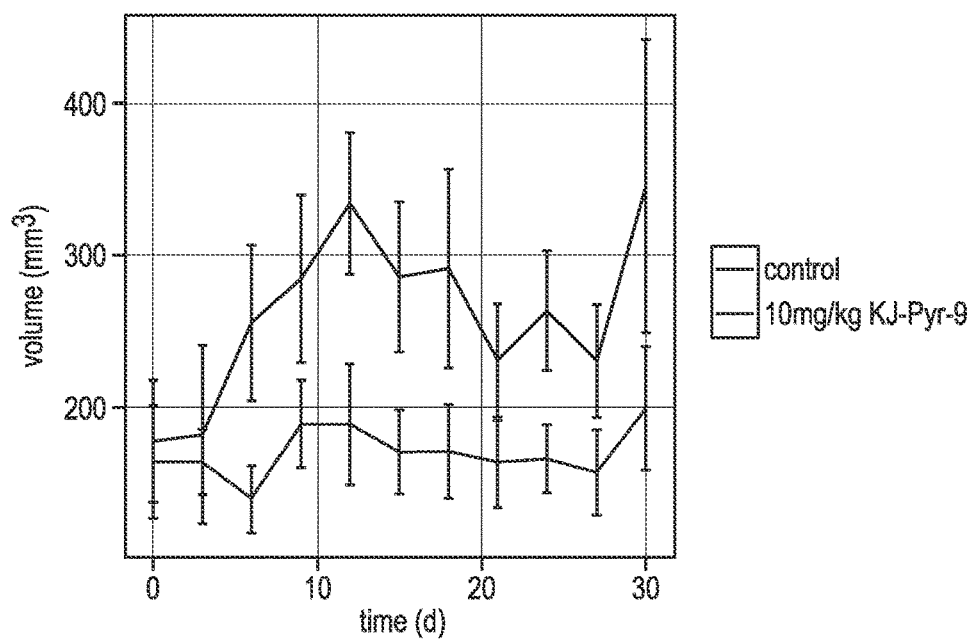

To test the in vivo effectiveness of KJ-Pyr-9, nude mice received a xenograft of MDA-MB-231 cells suspended in Matrigel and injected subcutaneously into the left and right flanks. When the tumors had reached an average volume of 100 mm³, mice were treated daily with 10 mg/kg KJ-Pyr-9 or vehicle control by intraperitoneal injection for 31 days. Inhibition of tumor growth by KJ-Pyr-9 was noted after eight days of treatment. By day 31, the tumor volume in the KJ-Pyr-9 treated animals had not increased significantly (FIG. 5). At the conclusion of the experiment the tumors were extracted and weighed. The weight measurements were in agreement with the volume determinations and confirmed the ability of KJ-Pyr-9 to halt tumor growth (FIG. 5). Treatment with KJ-Pyr-9 had no effect on the body weight of the animals.

In order to determine drug activity in tumor cells, protein lysates were prepared from frozen tumor samples and analyzed by Western blot. These blots showed that the expression of the Myc suppression target NDRG1 was significantly enhanced by treatment with KJ-Pyr-9. The degree of this enhancement varied between tumors. Immunofluorescent staining of NDRG1 and histological analysis suggested that the variability was caused by differences in the amounts of necrotic areas within the different tumors. These observations suggest that KJ-Pyr-9 gained access to the tumor tissue and inhibited the transcriptional activity of Myc.

Example 3. Some Materials and Methods Used in the Invention

Fluorescence Polarization Assay. His-tagged bHLH-LZ domains of MYC and MAX were expressed in *E. coli* and purified by His-trap. Fluorescence polarization assays were conducted as described in Kiessling et al., Chemistry & biology 13(7):745-751, 2006, except that 5-carboxyfluorescein was replaced with Alexa Fluor-594.

Renilla luciferase-based protein fragment complementation assay. HEK293 cells were grown in Dulbecco's Modified Eagle's Medium (DMEM) supplemented with 10% fetal bovine serum (FBS). The indicated Rluc-PCA expression constructs were transiently overexpressed in a 24-well plate format. 24 or 48 hrs post-transfection, confluent cells were treated with 20 µM KJ-Pyr-9. Following treatment, the growth medium was exchanged and cells were resuspended in phosphate buffered saline (PBS). Cell suspensions were transferred to white walled 96-well plates and were subjected to bioluminescence analysis using the LMax II 384 luminometer (Molecular Devices). Rluc bioluminescence signals were integrated for 10 sec following addition of the Rluc substrate benzyl-coelenterazine to intact cells (5 µM; Nanolight). For immuno-blot (IB) analyses, anti-Renilla Luciferase antibodies to detect either F[1]-fused (Millipore, MAB4410) or F[2]-fused (Millipore, MAB4400) hybrid proteins were used.

Assay for oncogenic transformation in cell culture. Oncogenic transformation was determined in cultures of chicken embryo fibroblasts (CEF) as previously described in Duff & Vogt, *Virology* 39:18-30, 1969; and Bos et al., *Genes & Dev.* 4:1677-1687, 1990. CEF were infected with a series of ten-fold dilutions of the indicated virus. Compounds were added to the nutrient agar overlay. Additional compound-containing overlay was added every 3 days until experimental end point. ATG-Myc was created by site-directed mutagenesis changing the CTG start codon of human c-Myc to ATG. It was then inserted in the retroviral expression vector RCAS(A).sfi (Aoki et al., *Proc. Natl. Acad. Sci. USA* 95:14950-14955, 1998).

Backscattering Interferometry data were collected on an instrument built by Molecular Sensing Inc., Nashville, Tenn. 37203. His-tagged maltose-binding protein fusions of the MYC and MAX bHLH-LZ domains were cloned and expressed in *E. coli*. These fusion proteins were purified by Ni-NTA column chromatography and buffer exchanged to 60 mM Tris/HCl (pH 7.5), 150 mM NaCl, 9 mM $MgCl_2$, 3 mM EDTA by dialysis in Slide-a-Lyzer cassettes (Thermo-Scientific). Constant amounts of MYC, MAX or MYC-MAX heterodimer were mixed with increasing amounts of KJ-Pyr-9 and analyzed by backscatter interferometry. The resulting changes in index of refraction were plotted and fitted to logistic curve to determine Kd.

Cell lines. The human cancer cell lines are NCI-H460 (ATCC) (large cell lung cancer), MDA-MB-231 (NCI) (adenocarcinoma of the breast), SUM-159PT (Asterand) (estrogen-independent breast cancer), and SW-480 (ATCC) (colorectal carcinoma). K-562, MOLT-4, and HL-60 are derived from chronic myeloid leukemia in blast crisis, acute lymphoblastic leukemia, and acute myeloid leukemia, respectively. Human immortalized fibroblasts (hFB) were provided by J. Troppmair (Medical University Innsbruck, Austria). Cell culture of quail (*Coturnix japonica*) embryo fibroblasts (QEF) and of the established quail cell lines Q8, QEF/MC29, VJ, QT6 was performed as described in Hartl et al., *Proc. Natl. Acad. Sci. USA* 106:5604-5609, 2009.

Cell proliferation assays. Assays used staining with the redox dye resazurin to measure cell viability according to the protocol of the manufacturer (Promega, Madison Wis.). Cells were seeded at $10^3$ per 100 µl well in 96 well-plates and grown in the presence of 2.5% FBS. MDA-MB-231 cells were cultured in DMEM, SUM-159PT cells in HAM's F12, and NCI-H460 cells in RPMI. MDA-MB-231 cells were exposed to KJ-Pyr-9 for 216 hrs with fresh compound-containing medium supplied at 120 and 192 hrs; SUM-159PT cells were exposed to the compound for 120 hrs and fresh medium with the appropriate compound concentrations supplied at 48 hrs; and NCI-H460 cells were grown with compound for 72 hrs.

Treatment of human cells K-562, MOLT-4, HL-60 and SW-480 and of quail cells with KJ-Pyr-9. For testing adherent cell types, $1.5 \times 10^5$ cells were seeded into MP-24 dishes and incubated over night at 37° C. The next day, the culture medium was replaced by 200 µl of ECB buffer containing 135 mM NaCl, 5 mM KCl, 10 mM HEPES pH 7.4, 1 mM $MgCl_2$, and 1 mM $CaCl_2$, and the KJ-Pyr-9 compound in 25 µM or 50 µM final concentrations (diluted from a stock solution in DMSO). Cells were incubated at 37° C. for 30 min. Then, 800 µl of cell culture medium containing the compound were added and the cells were further incubated for 24 hrs at 37° C. For cells grown in suspension (K-562, MOLT-4, HL-60), $1.5 \times 10^5$ cells were collected by centrifugation and resuspended in 200 µl of ECB buffer containing the compound. After 30-min incubation at 37° C., 800 µl of culture medium containing the compound were added, and cells incubated as above. Cell micrographs were taken 24 hrs after treatment with the compound.

Pharmacokinetics. Three mice were injected with 10 mg/kg KJ-Pyr-9 dissolved in 10:10:80 Tween-80:DMSO: 5% Dextrose/water intraperitoneally. At 4 hours concentrations of KJ-Pyr-9 in the plasma and in the brain were 3.5 and 12.4 µM respectively. Rats were dosed with 1 mg/kg i.v.; elimination half lives in plasma were approximately 1.84 h (rats).

Xenograft experiments. Ten 8-week old female nude mice (HSD:athymic nude) were injected with $5 \times 10^6$ MDA-MB-231 cells subcutaneously into left and right flanks. Cells were suspended in high concentration Matrigel (BD Biosciences) prior to injection. Xenograft tumors were allowed to grow until the average volume of the tumors reached 100 $mm^3$ as measured by external calipers. At this point, the mice were divided into two groups. One received 10 mg/kg KJ-PYR-9 and the other received vehicle only, dosed daily by intraperitoneal injection. Tumor volume and mouse weight were measured daily. Vehicle used in all cases was 10:10:80 DMSO:Tween-80:5% dextrose in water. The mice were treated for a period of 31 days. At the end of the experiment, the mice were euthanized and tumors excised. Tumors were weighed. Samples of each tumor were fixed in formalin for histology and frozen for Western blotting. All vertebrate experiments were conducted with the approval of the TSRI IACUC.

Immunofluorescent staining of NDRG1. Tumor tissues were fixed in 4% paraformaldehyde overnight, dehydrated and embedded in paraffin. All samples were sectioned at 5 µm. Processing of the sections for protein localization followed the Cell Signaling Immunofluorescence General Protocol. The primary antibody against NDRG1 was from Cell Signaling (#5196). Standard immunohistochemistry procedures for polyclonal primary antibodies were applied using the instruction from the Cell Signaling Immunofluorescence General Protocol. NDRG1 and nuclear staining were performed using FITC-conjugated goat anti-rabbit IgG (Sigma F-0382) as secondary antibody and were mounted in Pro-Long Gold Antifade with DAPI (Molecular Probes, #8961S). Micrographs were taken at 40× magnification (microscope objective) with a Hamamatsu digital CCD camera.

Statistical methods. Tumor volumes were calculated using $(length) \times (width)^2$. Tumor volumes were evaluated using Efron's Bootstrap (ISBN:0412042312) procedures as implemented in the R statistics program (Wu and Houghton, *J. Biopharma. Stat.* 19:755-762, 2009). Mean volumes and 90% confidence intervals were determined using bootstrap resampling with $10^6$ randomizations and graphed using the ggplot2 package (ISBN:0387981403). P-values were determined using the resampling permutation method with $10^6$ randomizations.

Example 4. Cell Proliferation Assay

K562, Daudi, NCI-H460, and/or HFF were all obtained from ATCC and grown as recommended by the manufacturer. One day before treatment, K562, Daudi, NCI-H460, and/or HFF were seeded in tissue-culture-treated 96-well plates at 3,000, 10,000, 3,000, 4,000 cells/well respectively, in 100 µl. Plates were incubated overnight at 37° C. Myc inhibitors were prepared in high grade DMSO (SIGMA, D8418). Serial dilutions or single dilutions of the compounds were prepared in serum free culture media, and added to cells (50 µl/well) in triplicate. After 3 days incubation at 37° C., cells proliferation was analyzed as follows: 10 µl of Dye Solution (CellTiter 96® Non-Radioactive Cell Proliferation Assay, Promega) was added to each well. Plates were incubated at 37° C. for 2-4H. Then 100 µl of Solubilization/Stop Solution was added to each well and plates were incubated at room temperature with agitation for 1H. Absorbance was recorded at 570 nm using a 96-well plate reader (Flexstation 3, Molecular Device). Data were analyzed in GraphPad prism, and $IC_{50}$ values were calculated when applied using non-linear regression fit (Log (inhibitor) vs. response—Variable slope equation).

Figure 8A:
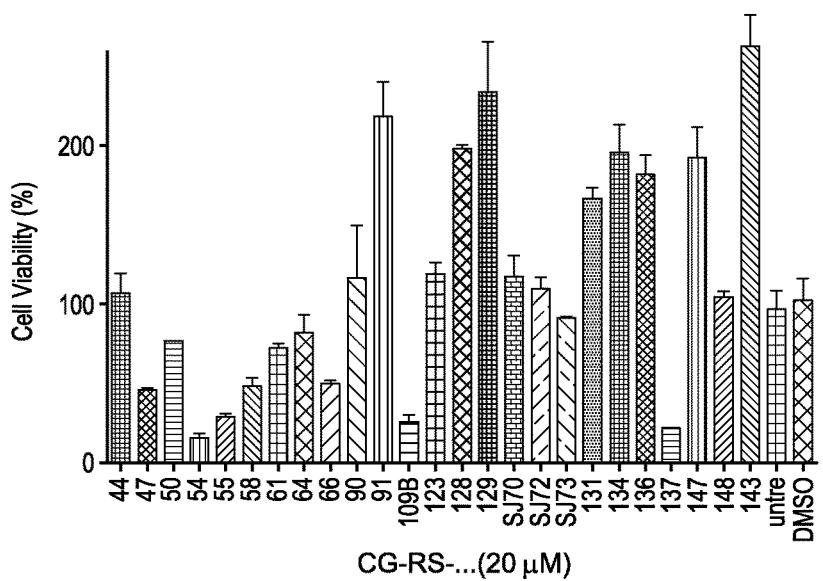
FIGS. 8A-8C show the cytotoxic efficacy of a first series of compounds (CG-RS-44 to -103), tested in 2 human cancer cell lines: Daudi (A) and K562 (B).
Figure 8B:
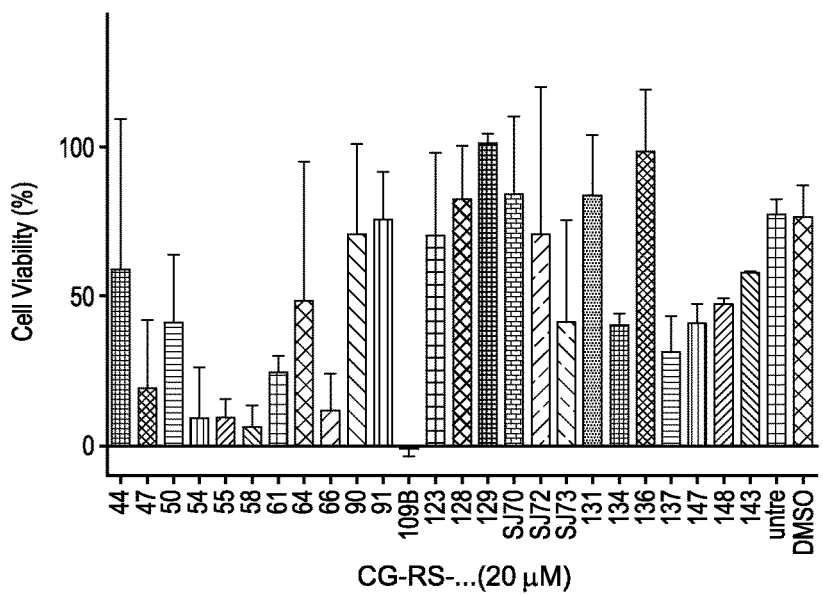
Figure 8C:
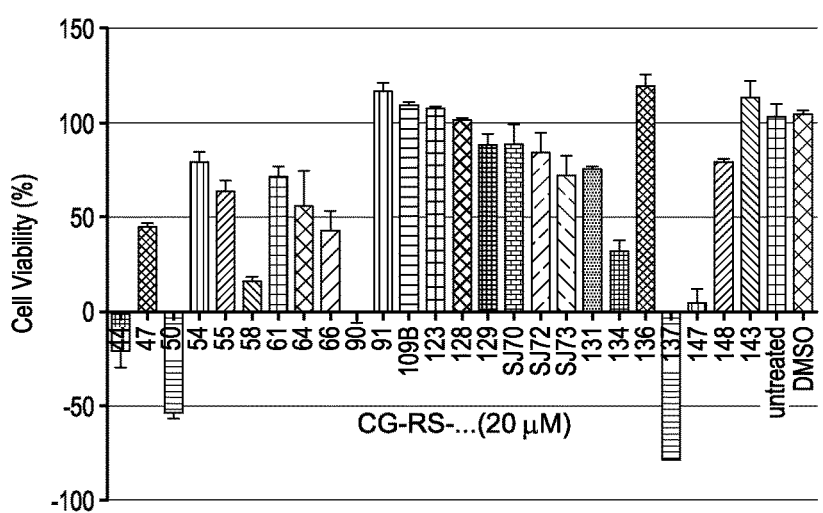
Figure 9A:
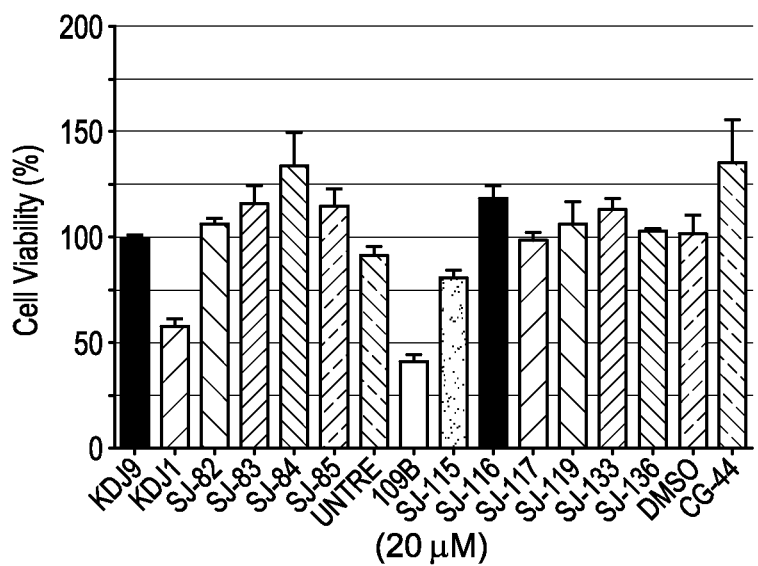
FIGS. 9A-9C show the cytotoxic efficacy of a second series of compounds, tested in Daudi (A), and K562 (B).
Figure 9B:
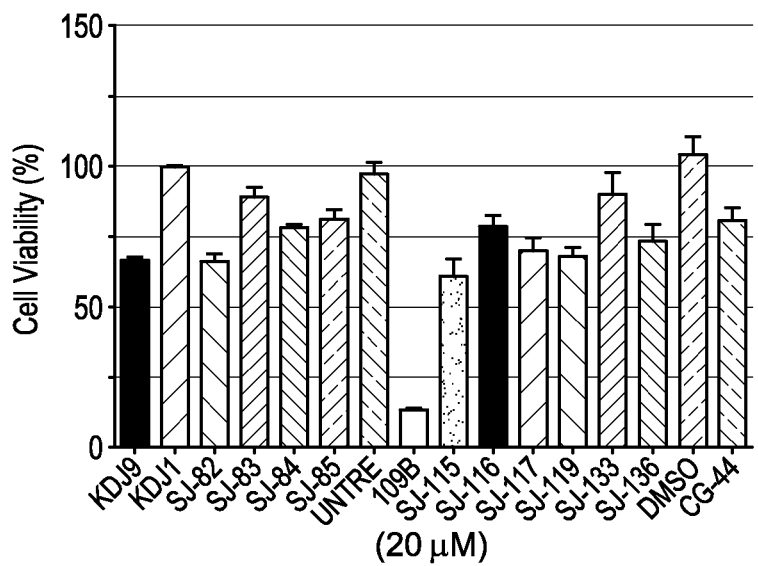
Figure 9C:
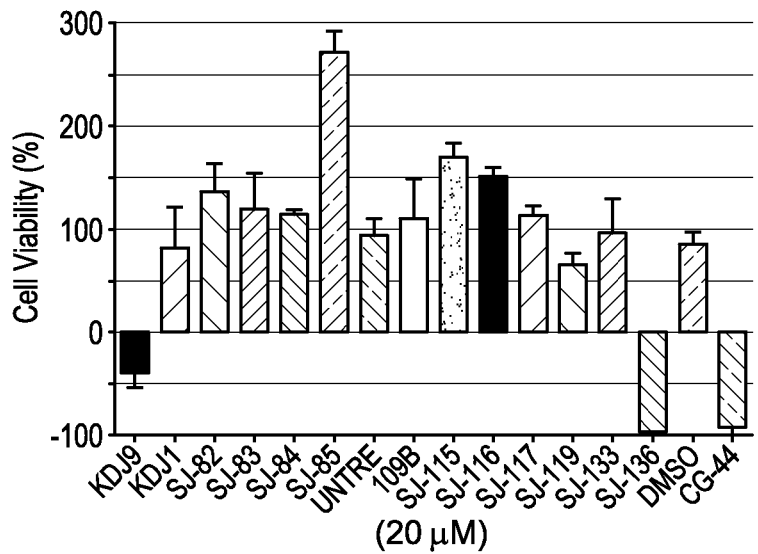
Figure 10:
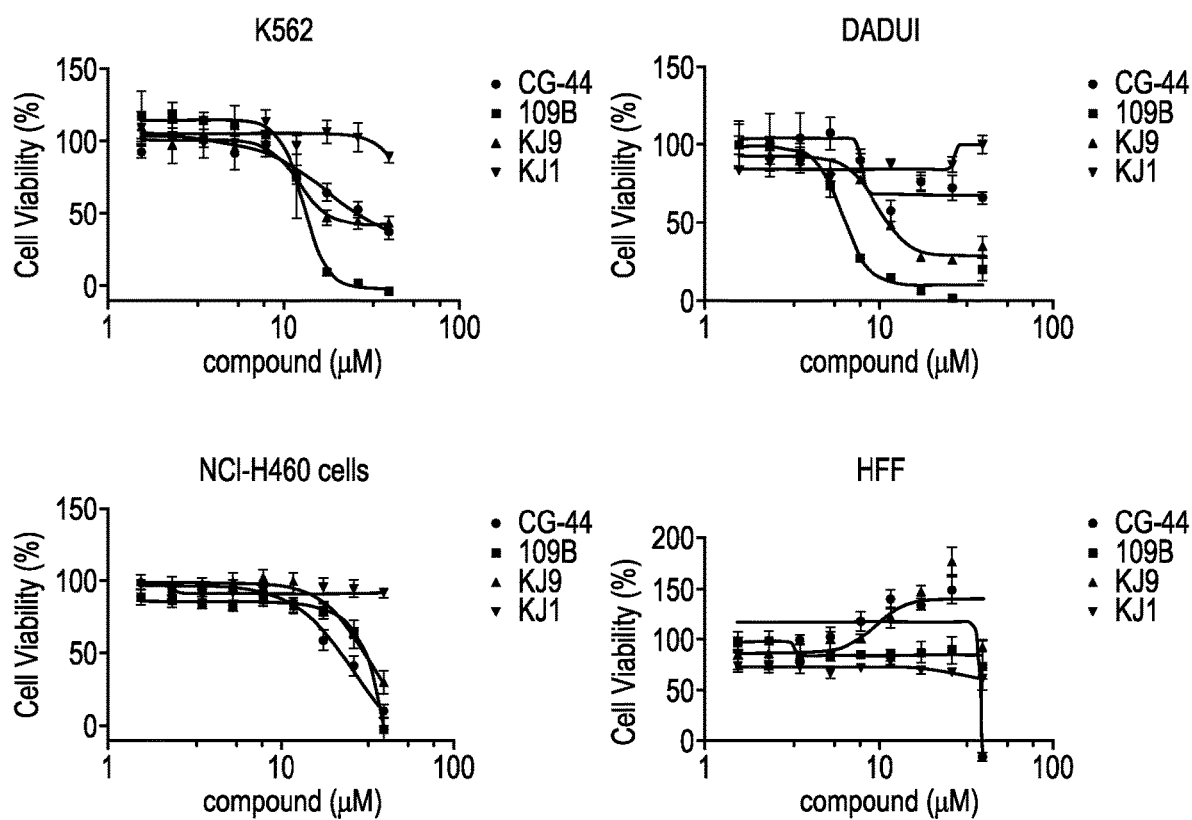
FIG. 10 shows the cell viability of four different cell lines when cultured in the presence of increasing concentrations of selected compounds.

The results for testing of the compounds at single dose (20 µM) are shown in FIGS. 8 and 9. Dose responses for selected compounds are shown in FIG. 10. HFF are normal cells that do not depend on Myc. They were used in this setting as control for non-specific cell killing. This illustrates the potential of Myc inhibitors as anti-cancer cell proliferation agents.

Figure 11:
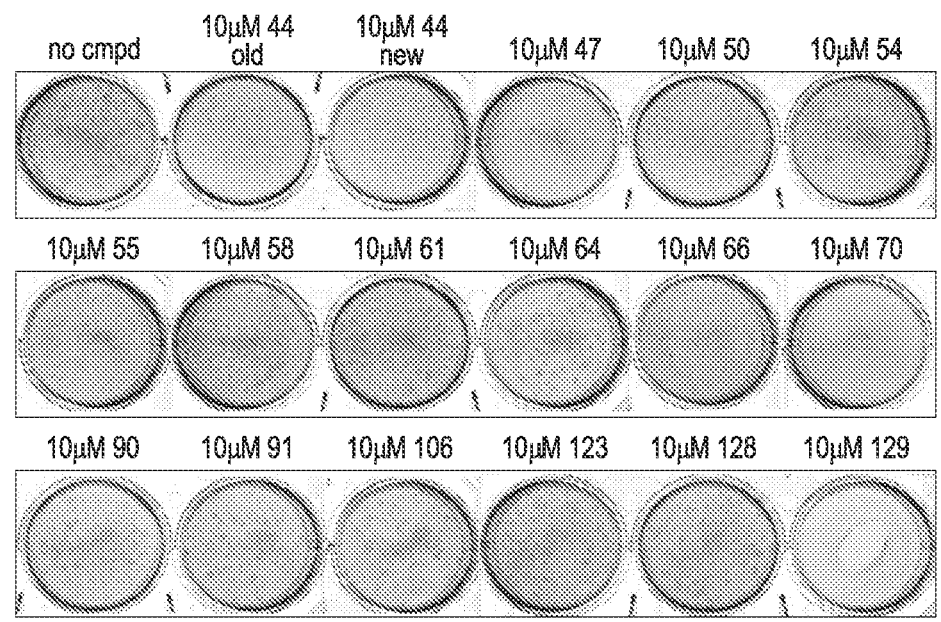
FIG. 11 shows the results of screening of KJ-Pyr-9 analog compounds for inhibition of ATG-Myc in CEF focus assays. As indicated in the figure, each compound was examined at a concentration of 10 µM. The last two digits listed after the compound concentration correspond to the internal designation of the different compounds. Two batches of Compound CG-RS-44 ("44" noted in the figure) were tested in the study.

Example 5. Validation of Inhibitory Activities of Some CG-RS-44 Derivative Compounds Using CEF focus assay on ATG-Myc, we first ascertained that compound CG-RS-44 (KJ-PYR-9) provides inhibition and specificity for ATG-Myc. The data indicate a dose-dependent inhibition at a concentration ranging from 0-20 µM of the compound (tested at 0, 1.25, 2.5, 5, 10, and 20 µM). We then examined activities of fifteen analogs of CG-RS-44 for inhibition of ATG-Myc focus formation. The results are shown in FIG. 11. Specifically, Compounds CG-RS-47, CG-RS-70 and CG-RS-129 (in addition to Compound CG-RS-44 itself) led to no foci formation at a concentration of 10 µM. These compounds completely inhibited focus formation at 10 µM making them work equal to or, possibly, better than CG-RS-44. In addition, Compounds CG-RS-50, CG-RS-54, CG-RS-55 and CG-RS-56 also showed some inhibiting activities, while there is no inhibition when Compound CG-RS-58, -61, -64, -90, -91, -106, -123 or -128 was used. Further, it was observed that there is a slight decrease in cell growth for Compounds CG-RS-70 or -129. Myc-inhibitory activities of several compounds were also examined via measuring IC50 values in the CEF assay. The results from this study showed that Compound CG-RS-44 inhibited ATG-Myc focus formation better than all analogs tested, including Compounds CG-RS-47, -70, and -10913.

The specificity of the inhibitory activities of the analog compounds was also examined. In brief, Compounds CG-RS-47, -70, -129 and -109B were analyzed in CEFI specificity assay for their inhibitory activities on several Myc analogs, including v-src, 111047R and v-jun. The results indicate that these CG-RS-44 derivative compounds all displayed some degrees of specificity for inhibiting Myc over the Myc analogs.

Example 6. Synthesis of Aldol Products and Target Compounds

Synthesis of CG-RS-40

The following compounds 4-formylbenzamide (7.0 g, 47 mmol) and 2-acetylfuran (3.9 mL, 39 mmol) were taken in a RB flask under nitrogen atmosphere. THF (280 mL) was added and then powdered LiOH (934 mg, 39 mmol). The resulting turbid mixture was stirred at room temperature overnight. At this time LC showed trace of 2-acetylfuran, and mainly the desired product and 4-formylbenzamide (~20%). Quenched with 2.2 mL of acetic acid in 20 mL of water. Water and ethyl acetate were added, the layers were separated. The aqueous layer was extracted with 20% IPA in ethyl acetate twice. The organic portions were combined and concentrated. The resulting solids were treated with ether (70 mL), heated and decanted. This was repeated two more times. The solids were triturated with 10% MeOH/DCM (30 mL), filtered and washed with 10% MeOH/DCM (10 mL). The solids weigh 4.4 g. The filtrates were concentrated and purified in an isco 220 g silica cartridge. This resulted additional 550 mg as white solids. ESI (m/z)=(M+H) 242.

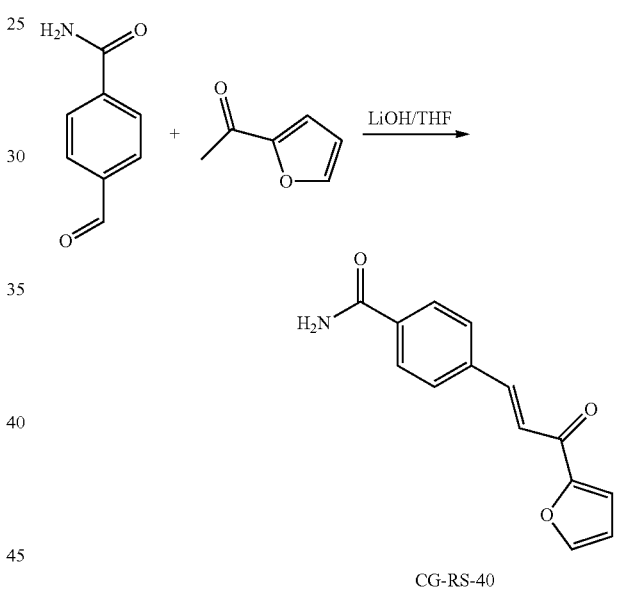

CG-RS-40

Synthesis of CG-RS-48

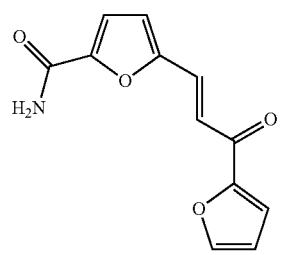 [SMILES: NC(=O)c1ccc(/C=C/C(=O)c2ccco2)o1]

The following compounds 5-formylfuran-2-carboxamide (2.6 g, 18 mmol) and 2-acetylfuran (1.5 mL, 15 mmol) were taken in a RB flask under nitrogen atmosphere. THF (106 mL) was added and then powdered LiOH (360 mg, 15 mmol). The resulting turbid mixture was stirred at room temperature overnight. After 28 h, quenched with 1 mL of acetic acid in 10 mL of water. Additional water and ethyl acetate were added, the layers were separated. The aqueous layer was extracted with 20% IPA in ethyl acetate (100 mL) twice. The organic portions were combined, washed with water, brine, dried (Na2SO4), filtered and concentrated. The resulting solids were triturated with 10% MeOH/DCM (30 mL), filtered and washed with 10% MeOH/DCM (10 mL×3). The dried solids weigh 2.0 g about 90% pure. No further purification was attempted. ESI (m/z)=(M+H) 232.

Synthesis of 5-formylfuran-2-carboxamide

5-Hydroxymethylfuran-2-carboxamide (470 mg, 3.3 mmol) was taken in DCM (6 mL) and THF (6 mL) at room temperature and Des-Martin reagent (1.6 g, 3.7 mmol) was added. Stirring continued overnight. At this time TLC showed mainly the desired product (non-polar compared to starting material). Usual aqueous work up and isolation in methanol led to 300 mg of the desired product.

Synthesis of 5-hydroxymethylfuran-2-carboxamide

In a pressure reactor was taken methyl (5-hydroxymethyl) furancarboxylate (12 g), MeOH (50 mL), and concentrated NH$_4$OH (70 mL). Heated to 100° C., and after 24 h, TLC showed mainly two polar spots and no starting material remains. Concentrated in a rotary evaporator, the resulting solids were taken in ~55 mL of IPA and heated to dissolve completely. Cooled down to room temperature, the solids started separate out, filtered and dried (2.4 g), Then the mother liquor was concentrated to half the volume and 1.3 g of second crop was obtained.

Synthesis of CG-RS-86

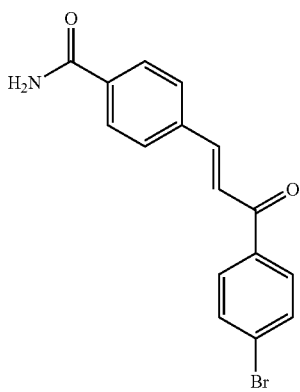 [SMILES: NC(=O)c1ccc(/C=C/C(=O)c2ccc(Br)cc2)cc1]

The following compounds 4-formylbenzamide (1.49 g, 10 mmol) and 4'-bromoacetophenone (1.7 g, 8.3 mmol) were taken in a RB flask under nitrogen atmosphere. THF (60 mL) was added and then powdered LiOH (200 mg, 8.3 mmol). The resulting turbid mixture was stirred at room temperature overnight. At this time LC showed major as the desired product. Aqueous acetic acid was added to quench the reaction. Water and ethyl acetate were added, the layers were separated. The aqueous layer was extracted with 20% IPA in ethyl acetate twice. The organic portions were combined and washed with water. Concentrated to afford white solids; the resulting solids were treated with ether (50 mL), sonicated and set aside for precipitation. Filtered and washed with more ether (60 mL×3), dried 1.54 g which is 90-95% pure. No further purification was done. ESI (m/z)=(M+H) 330.

Synthesis of CG-RS-89

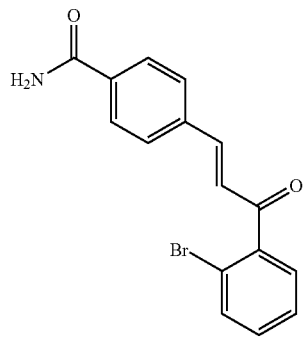 [SMILES: NC(=O)c1ccc(/C=C/C(=O)c2ccccc2Br)cc1]

The reaction of 4-formylbenzamide (2.3 g, 15.6 mmol) and 2'-bromoacetophenone (2.4 g, 12 mmol) following similar procedure as described in the synthesis of CG-RS-86 gave 1.83 g of the product. ESI (m/z)=(M+H) 330.

Synthesis of CG-RS-105

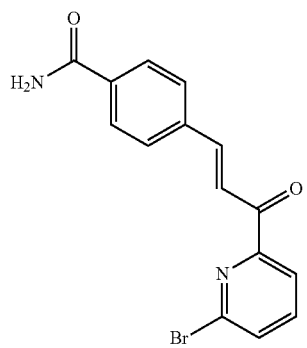 [SMILES: NC(=O)c1ccc(/C=C/C(=O)c2cccc(Br)n2)cc1]

The reaction of 4-formylbenzamide (1.5 g, 10 mmol) and 6-bromopyridin-2-yl methyl ketone (1.5 g, 7.5 mmol) following similar procedure as described in the synthesis of CG-RS-86 gave 650 mg of the aldol product. ESI (m/z) (M+H) 331.

Synthesis of CG-RS-107

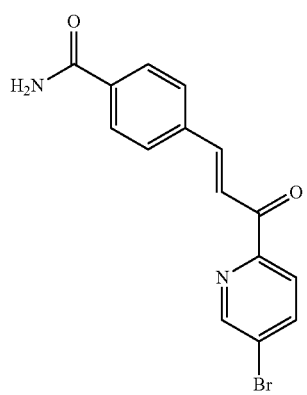 [SMILES: NC(=O)c1ccc(/C=C/C(=O)c2ccc(Br)cn2)cc1]

The reaction of 4-formylbenzamide (745 mg, 5 mmol) and 5-bromopyridin-2-yl methyl ketone (800 mg, 4 mmol) following similar procedure as described in the synthesis of CG-RS-86 gave 320 mg of the aldol product. ESI (m/z)= (M+H) 331.

Synthesis of CG-RS-112

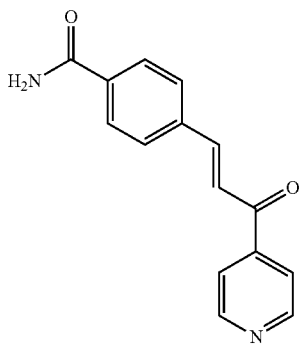 [SMILES: NC(=O)c1ccc(/C=C/C(=O)c2ccncc2)cc1]

The reaction of 4-formylbenzamide (450 mg, 3 mmol) and 4-acetylpyridine (290 mg, 2.4 mmol) following similar procedure as described in the synthesis of CG-RS-86 gave 300 mg of the aldol product. ESI (m/z)=(M+H) 253.

Synthesis of CG-RS-122

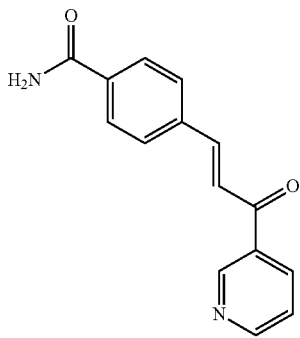 [SMILES: NC(=O)c1ccc(/C=C/C(=O)c2cccnc2)cc1]

The reaction of 4-formylbenzamide (1 g, 6.7 mmol) and 3-acetylpyridine (650 mg, 5.4 mmol) following similar procedure as described in the synthesis of CG-RS-86 gave 450 mg of the aldol product. ESI (m/z)=(M+H) 253.

Synthesis of CG-RS-124

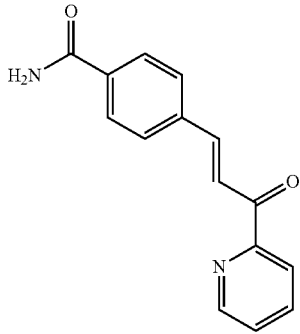 [SMILES: NC(=O)c1ccc(/C=C/C(=O)c2ccccn2)cc1]

The reaction of 4-formylbenzamide (1 g, 6.7 mmol) and 2-acetylpyridine (650 mg, 5.4 mmol) following similar procedure as described in the synthesis of CG-RS-86 gave 600 mg of the aldol product. ESI (m/z)=(M+H) 253.

Synthesis of CG-RS-145

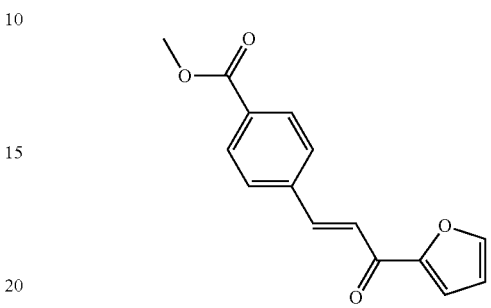

The following compounds methyl 4-formylbenzoate (1.64 g, 10 mmol) and 2-acetylfuran (0.84 mL, 8.3 mmol) were taken in a RB flask under nitrogen atmosphere. THF (50 mL) was added and then powdered LiOH (200 mg, 8.3 mmol). The resulting turbid mixture was stirred at room temperature 5 h. At this time LC showed mainly the starting materials, hence few mL of MeOH was added and stirring continued for an additional 3 h. Aqueous acetic acid was added to quench the reaction. Water and ethyl acetate were added, the layers were separated. The aqueous layer was extracted with ethyl acetate. The combined organic portion was washed with water twice, dried ($MgSO_4$), filtered and concentrated to obtain 2.8 g of the crude product. Purified using 220 g silica cartridge. ESI (m/z)=(M+H) 257.

Generalized Procedure for the Synthesis of Target Compounds:

Synthesis of CG-RS-44

The solids CG-RS-40 and CG-RS-32 were taken in a RB flask under nitrogen. DMF was added and the solids become reddish cloudy solution, then acetic acid was added becomes light yellow color. Finally $NH_4OAc$ was added, the solution becomes slightly reddish and somewhat clear solution. Placed in a preheated oil bath at 50° C. and then heated to 90° C., maintained at this temperature for 2 h. At this time, LC showed mainly the desired product and no starting material remains. Heating off, allowed to cool down to room temperature. Quenched by adding excess water, and stirred for a while. Solids separate out and filtered and washed with water several times. The solids were dissolved in minimum amount of DCM and loaded on to a 220 g silica cartridge, eluted with 100% DCM up to 5 minutes, then increased to 0-5% MeOH/DCM from 5 to 25 minutes, maintained 5% MeOH/DCM from 25 to 45 minutes. Fractions from 150 to 173 were combined and concentrated, few mL of MeOH was added and triturated, the solids were filtered and dried, brown solids 1.5 g. Data: $^1$H NMR (600 MHz, DMSO-$d_6$) δ ppm 6.72 (dd, J=3.51, 1.76 Hz, 1H) 7.39 (d, J=3.22 Hz, 1H) 7.48 (s, 1H) 7.92 (s, 1H) 8.02-8.07 (m, 2H) 8.08-8.16 (m, 4H) 8.29-8.40 (m, 3H) 8.57 (d, J=9.08 Hz, 2H). ESI (m/z)=(M+H) 386.

Representative scheme for the synthesis of target compounds:

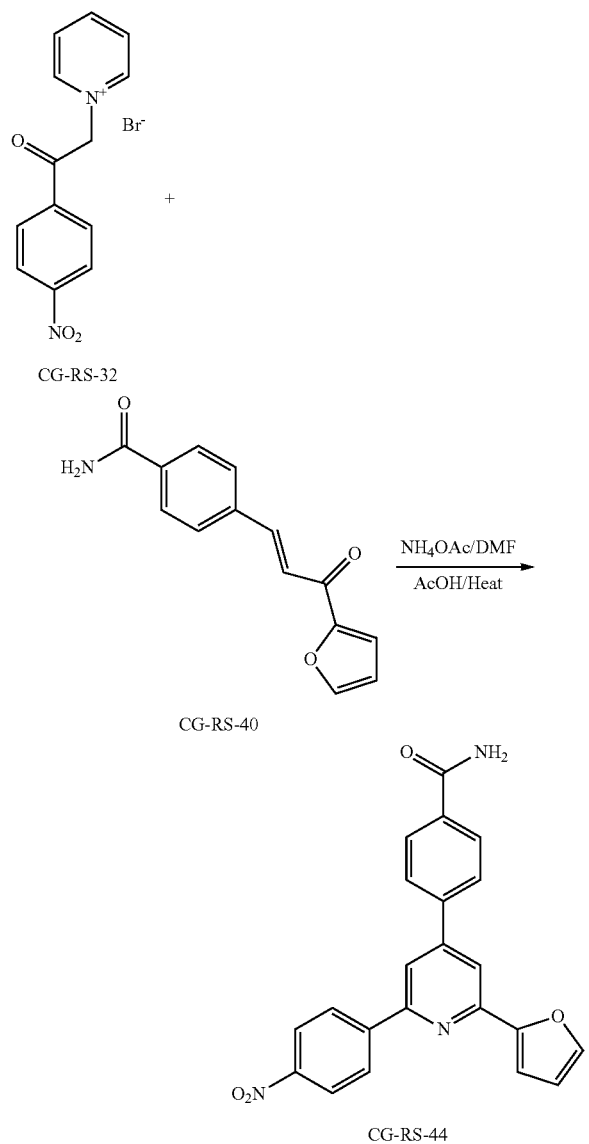

Synthesis of CG-RS-50

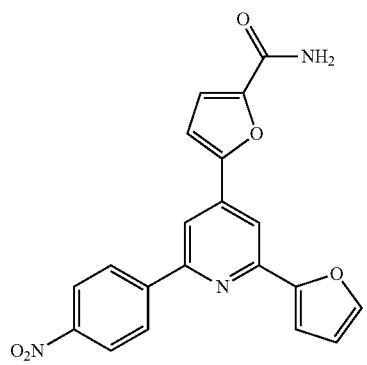 [SMILES: NC(=O)c1ccc(-c2cc(-c3ccc([N+](=O)[O-])cc3)nc(-c3ccco3)c2)o1]

The solids CG-RS-48 (2.0 g, 8.6 mmol) and CG-RS-32 (3.1 g, 9.5 mmol) were taken in a RB flask under nitrogen. DMF (40 mL) was added, followed by acetic acid (20 mL) and then NH$_4$OAc (16.6 g, 215 mmol) was added. Placed in a preheated oil bath at 50° C. and then heated to 90° C., maintained at this temperature for 1.5 h. At this time, LC showed mainly the desired product and no starting material remains. Heating off, allowed to cool down to room temperature. Quenched by adding excess water, and stirred for a while. Solids separate out and filtered and washed with water several times. Dried under high vacuum and then the solids were dissolved in DMF (=5 mL) and loaded on to a 220 g silica cartridge, eluted with 100% DCM up to 10 minutes, then increased to 0-4% MeOH/DCM from 10 to 30 minutes, maintained 4% MeOH/DCM from 30 to 45 minutes. Fractions from 185 to 230 were combined and concentrated, to the residue isopropanol (~50 mL) was added and triturated, the solids were filtered and dried, yellow solids 1.04 g. Data: $^1$H NMR (600 MHz, DMSO-d$_6$) δ ppm 6.73 (dd, J=3.51, 1.76 Hz, 1H) 7.25 (d, J=3.51 Hz, 1H) 7.35 (d, J=2.63 Hz, 1H) 7.64 (d, J=3.51 Hz, 1H) 7.67 (br. s., 1H) 7.92 (s, 1H) 8.18-8.28 (m, 2H) 8.38 (d, J=8.78 Hz, 2H) 8.46 (s, 1H) 8.54 (d, J=9.08 Hz, 2H). ESI (m/z)=(M+H) 376.

Synthesis of CG-RS-47

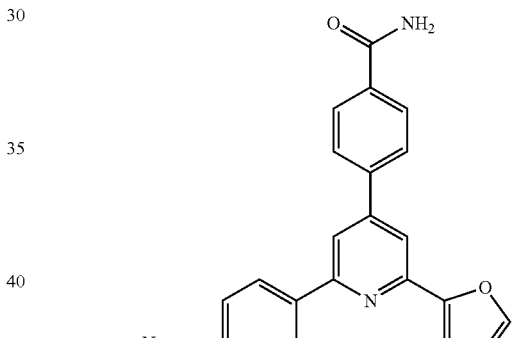

The solids CG-RS-40 (241 mg, 1 mmol) and CG-RS-46 (333 mg, 1.1 mmol) were taken in a RB flask under nitrogen. DMF (5 mL) was added, followed by acetic acid (2.5 mL) and then NH$_4$OAc (2.3 g, 25 mmol) was added. Placed in a preheated oil bath at 50° C. and then heated to 90° C., maintained at this temperature for 1 h. At this time, LC showed mainly the desired product. Heating off, allowed to cool down to room temperature. Quenched by adding excess water, and stirred for a while. Solids separate out and filtered and washed with water several times. Washed with ether (30 mL×3), dried under high vacuum. The solids were dissolved in a minimum amount of DCM and loaded on to a 40 g silica cartridge, eluted with 0-5% MeOH/DCM from 0-20 minutes. Fractions from 15 to 55 were combined and concentrated, brown solids 120 mg. Data: $^1$H NMR (600 MHz, DMSO-do) 6 ppm 6.72 (dd, J=3.22, 1.76 Hz, 1H) 7.38 (d, J=3.51 Hz, 1H) 7.47 (br. s., 1H) 7.86-7.94 (m, 1H) 7.96-8.16 (m, 8H) 8.32 (d, J=1.17 Hz, 1H) 8.51 (d, J=8.49 Hz, 2H). ESI (m/z)=(M+H) 366.

Synthesis of CG-RS-54

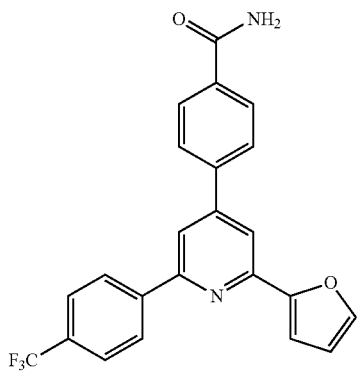 [SMILES: NC(=O)c1ccc(-c2cc(-c3ccc(C(F)(F)F)cc3)nc(-c3ccco3)c2)cc1]

The solids CG-RS-40 (150 mg, 0.62 mmol) and CG-RS-52 (237 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 2 h. At this time, LC showed mainly the desired product. Heating off, allowed to cool down to room temperature. Quenched by adding excess water, and stirred for a while. Solids separate out and filtered and washed with water several times, dried. The solids were taken in DCM and then IPA (10 mL) was added, concentrated in a rotary evaporator. The dark residue was dissolved in a minimum amount of DCM and loaded on to a 40 g silica cartridge, eluted with 100% DCM till 10 minutes, 0-4% MeOH/DCM from 10-25 minutes and 4% MeOH/DCM from 25-30 minutes. Fractions from 49 to 55 were combined and concentrated, light brown solids 120 mg. Data: $^1$H NMR (600 MHz, DMSO-d$_6$) δ ppm 6.72 (d, J=1.76 Hz, 1H) 7.37 (d, J=2.93 Hz, 1H) 7.47 (br. s., 1H) 7.82-7.97 (m, 3H) 8.00-8.19 (m, 6H) 8.29 (s, 1H) 8.51 (d, J=7.90 Hz, 2H). ESI (m/z)=(M+H) 409.

Synthesis of CG-RS-55

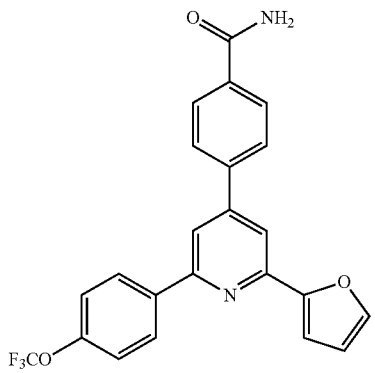

The solids CG-RS-40 (150 mg, 0.62 mmol) and CG-RS-53 (246 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 4 h. At this time, LC showed mainly the desired product. Heating off, allowed to cool down to room temperature. Workup and purification procedures are similar to CG-RS-54, light yellow solids, 95 mg. Data: NMR (600 MHz, DMSO-d$_6$) δ ppm 6.71 (dd, J=3.37, 1.61 Hz, 1H) 7.35 (d, J=3.22 Hz, 1H) 7.51 (d, J=8.20 Hz, 3H) 7.90 (s, 1H) 7.99-8.17 (m, 6H) 8.22 (s, 1H) 8.41 (d, J=8.78 Hz, 2H). ESI (m/z)=(M+H) 425.

Synthesis of CG-RS-58

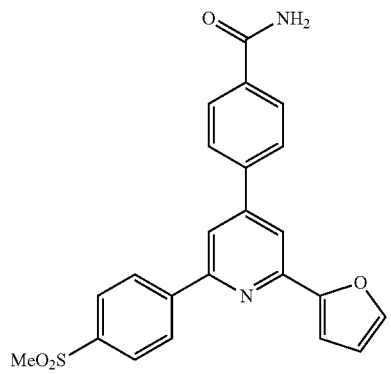 [SMILES: CS(=O)(=O)c1ccc(-c2cc(-c3ccc(C(N)=O)cc3)cc(-c3ccco3)n2)cc1]

The solids CG-RS-40 (150 mg, 0.62 mmol) and CG-RS-57 (243 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 1 h. At this time, LC showed mainly the desired product. Heating off, allowed to cool down to room temperature Workup and purification procedures are similar to CG-RS-54, light yellow solids, 125 mg. Data: $^1$H NMR (600 MHz, DMSO-d$_6$) δ ppm 3.28 (d, J=10.54 Hz, 3H) 6.72 (br. s., 1H) 7.39 (d, J=3.22 Hz, 1H) 7.43-7.57 (m, 1H) 7.92 (s, 1H) 7.99-8.22 (m, 8H) 8.31 (s, 1H) 8.55 (d, J=8.20 Hz, 2H). ESI (m/z)=(M+H) 419.

Synthesis of CG-RS-61

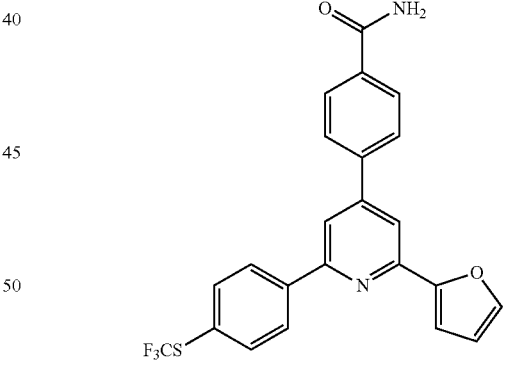

The solids CG-RS-40 (150 mg, 0.62 mmol) and CG-RS-60 (258 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 2 h. At this time, LC showed mainly the desired product. Heating off, allowed to cool down to room temperature Workup and purification procedures are similar to CG-RS-54, brown solids, 120 mg. Data: $^1$H NMR (600 MHz, DMSO-d$_6$) δ ppm 6.62-6.77 (m, 1H) 7.37 (d, J=2.93 Hz, 1H) 7.47 (br. s., 1H) 7.81-7.97 (m, 3H) 8.00-8.19 (m, 6H) 8.27 (s, 1H) 8.43 (d, J=8.20 Hz, 2H). ESI (m/z)=(M+H) 441.

Synthesis of CG-RS-64

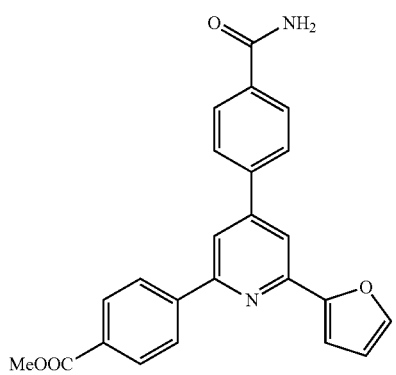 [SMILES: COC(=O)c1ccc(-c2cc(-c3ccc(C(N)=O)cc3)cc(-c3ccco3)n2)cc1]

The solids CG-RS-40 (150 mg, 0.62 mmol) and CG-RS-63 (229 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 1 h. At this time, LC showed mainly the desired product. Heating off, allowed to cool down to room temperature Workup and purification procedures are similar to CG-RS-54, light brown solids, 100 mg. Data: $^1$H NMR (600 MHz, DMSO-d$_6$) δ ppm 3.89 (s, 3H) 6.63-6.81 (m, 1H) 7.37 (d, J=3.51 Hz, 1H) 7.42-7.53 (m, 1H) 7.91 (s, 1H) 7.99-8.19 (m, 8H) 8.28 (s, 1H) 8.45 (d, J=8.49 Hz, 2H). ESI (m/z)=(M+H) 399.

Synthesis of CG-RS-66

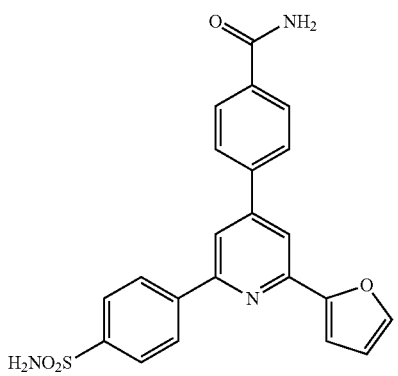 [SMILES: NC(=O)c1ccc(-c2cc(-c3ccc(S(N)(=O)=O)cc3)nc(-c3ccco3)c2)cc1]

The solids CG-RS-40 (150 mg, 0.62 mmol) and CG-RS-65 (243 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 2 h. At this time, LC showed mainly the desired product. Heating off, allowed to cool down to room temperature. Quenched by adding excess water, and stirred for a while. Solids separate out, filtered and washed with water several times, washed with ether three times, dried. The residue was dissolved in DMF (~1 mL) and loaded on to a 40 g silica cartridge, eluted with 100% DCM till 5 minutes, 0-15% MeOH/DCM from 5-30 minutes. Fractions from 49 to 54 were combined and concentrated, light brown solids 70 mg. Data: $^1$H NMR (600 MHz, DMSO-d$_6$) δ ppm 6.72 (d, J=1.46 Hz, 1H) 7.38 (d, J=3.22 Hz, 1H) 7.44 (s, 3H) 7.88-7.99 (m, 3H) 8.00-8.15 (m, 6H) 8.27 (s, 1H) 8.48 (d, J=8.49 Hz, 2H). ESI (m/z)=(M+H) 420.

Synthesis of CG-RS-67A and CG-RS-67B

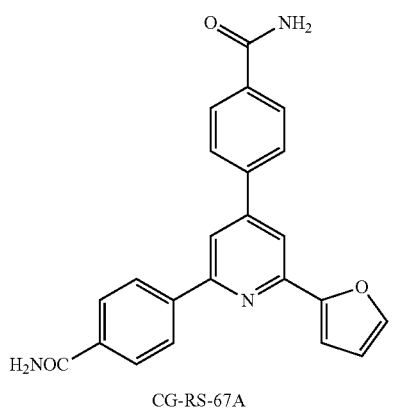

CG-RS-67A

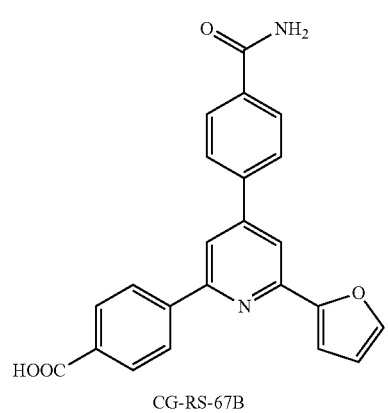

CG-RS-67B

CG-RS-64 (50 mg, 0.12 mmol) was taken in a pressure vessel, MeOH (2 mL) and Conc. NH$_4$OH (2 mL) were added. The resulting solution was heated to 100° C. and maintained overnight. At this time LC showed both acid and amide, no ester remains. The contents were concentrated, the residue was taken in DCM and few drops of acetic acid were added, concentrated again. The residue was purified in a 12 g silica cartridge, eluted with 100% DCM till 5 minutes, and 0-20% MeOH/DCM from 5 to 30 minutes, 20% MeOH/DCM from 30 to 35 minutes.

Top fractions are amide (weighs 10 mg). Data: CG-RS-67A: $^1$H NMR (600 MHz, DMSO-d$_6$) μ ppm 6.71 (br. s., 1H) 7.37 (s, 1H) 7.41-7.50 (m, 2H) 7.90 (s, 1H) 7.98-8.15 (m, 8H) 8.25 (s, 1H) 8.37 (d, J=7.61 Hz, 2H). ESI (m/z)=(M+H) 384. The polar fractions are acid (weighs 19 mg). CG-RS-67B: $^1$H NMR (600 MHz, DMSO-d$_6$) δ ppm 6.68-6.75 (m, 1H) 7.37 (d, J=2.64 Hz, 1H) 7.46 (br. s., 1H) 7.91 (s, 1H) 8.00-8.15 (m, 8H) 8.26 (s, 1H) 8.41 (d, J=8.20 Hz, 2H). ESI (m/z)=(M+H) 385.

Synthesis of CG-RS-70

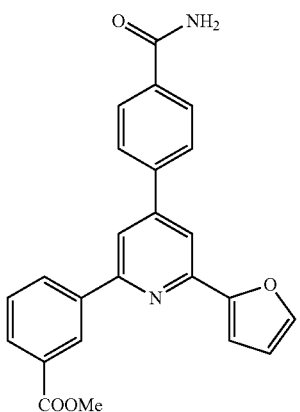 [SMILES: COC(=O)c1cccc(-c2cc(-c3ccc(C(N)=O)cc3)cc(-c3ccco3)n2)c1]

The solids CG-RS-40 (262 mg, 1.1 mmol) and CG-RS-69 (400 mg, 1.1 mmol) were taken in a RB flask under nitrogen. DMF (6 mL) was added, followed by acetic acid (2 mL) and then NH$_4$OAc (2.1 g, 27.5 mmol) was added. Placed in a preheated oil bath at 50° C. and then heated to 90° C., maintained at this temperature for 3 h. At this time, LC showed mainly the desired product. Heating off, allowed to cool down to room temperature. Quenched by adding excess water, and stirred for a while. Solids separate out and filtered and washed with water several times, dried. The solids were taken in DCM and then IPA (10 mL) was added, concentrated in a rotary evaporator. The dark residue was dissolved in a minimum amount of DCM and loaded on to a 40 g silica cartridge, eluted with 100% DCM till 10 minutes, 0-5% MeOH/DCM from 10-25 minutes and 5% MeOH/DCM from 25-30 minutes. The fractions containing product were combined and concentrated, light brown solids 20 mg, and slightly impure 100 mg. Data: $^1$H NMR (600 MHz, DMSO-d$_6$) δ ppm 3.90 (s, 3H) 6.67-6.77 (m, 1H) 7.34 (d, J=2.64 Hz, 1H) 7.46 (br. s., 1H) 7.69 (t, 1=7.76 Hz, 1H) 7.91 (s, 1H) 8.00-8.15 (m, 7H) 8.23 (s, 1H) 8.55 (d, J=7.61 Hz, 1H) 8.81 (s, 1H). ESI (m/z)=(M+H) 399.

Synthesis of CG-RS-72

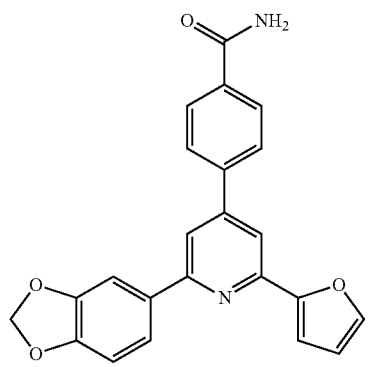 [SMILES: NC(=O)c1ccc(-c2cc(-c3ccc4c(c3)OCO4)nc(-c3ccco3)c2)cc1]

The solids CG-RS-40 (150 mg, 0.62 mmol) and CG-RS-71 (218 mg, 0.68 mmol) were taken in a RB flask under nitrogen. DMF (4 mL) was added, followed by acetic acid (2 mL) and then NH$_4$OAc (1.2 g, 15.5 mmol) was added. Placed in a preheated oil bath at 50° C. and then heated to 90° C., maintained at this temperature for 3 h. At this time, LC showed mainly the desired product. Heating off, allowed to cool down to room temperature. Workup and purification procedures are similar to CG-RS-54, light brown solids, 120 mg. Data: $^1$H NMR (600 MHz, DMSO-d$_6$) μ ppm 6.09 (s, 2H) 6.69 (dd, J=3.22, 1.76 Hz, 1H) 7.05 (d, J=8.20 Hz, 1H) 7.32 (d, J=2.93 Hz, 1H) 7.45 (br. s., 1H) 7.84-7.90 (m, 3H) 7.92 (d, J=1.17 Hz, 1H) 7.99-8.08 (m, 4H) 8.10 (s, 2H). ESI (m/z)=(M+H) 385.

Synthesis of CG-RS-73

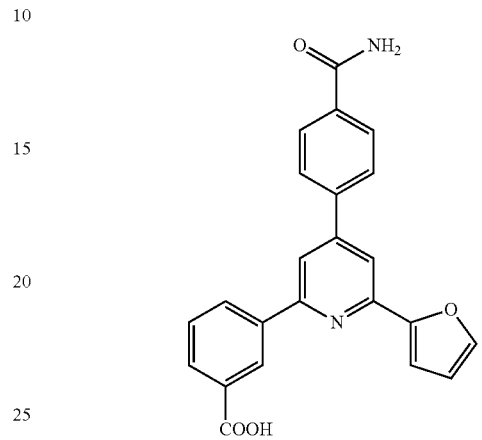

CG-RS-70 (100 mg, 0.24 mmol) was taken in a pressure vessel, MeOH (5 mL) and Conc. NH$_4$OH (5 mL) were added. The resulting solution was heated to 100° C. and maintained overnight. At this time LC showed both acid and amide, no ester remains. The contents were concentrated, the residue was taken in IPA and few drops of acetic acid were added, concentrated again. The residue was purified in a 40 g silica cartridge, eluted with 100% DCM till 5 minutes, and 0-20% MeOH/DCM from 5 to 25 minutes, ramp up to 30% MeOH/DCM from 25 to 32 minutes.

Fractions 48-60 contain both amide and acid, hence combined and concentrated, taken to next step. Few fractions containing acid alone were combined and concentrated to obtain 8 mg of the acid. Data: $^1$H NMR (600 MHz, DMSO-d$_6$) δ ppm 6.71 (br. s., 1H) 6.75-7.11 (m, 1H) 7.34 (d, J=3.81 Hz, 1 II) 7.46 (br. s., 1H) 7.61-7.72 (m, 1H) 7.91 (s, 1H) 8.00-8.14 (m, 7H) 8.22 (s, 1H) 8.51 (s, 1H) 8.79 (s, 1H). ESI (m/z)=(M+H) 385.

Synthesis of CG-RS-75

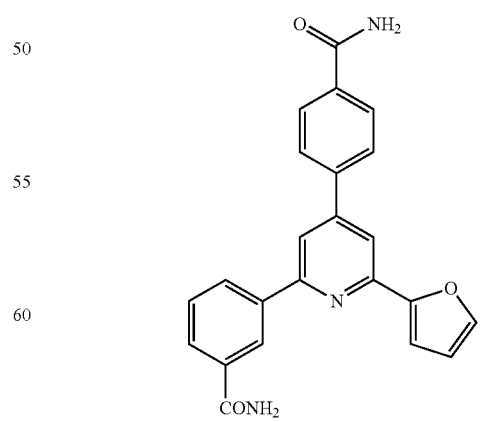

The mixture of acid and amide from CG-RS-73 (60 mg) was taken in a mixture of THF (4 mL) and MeOH (1 mL)

at room temperature under nitrogen. Trimethylsilyldiazomethane (2M solution in ether, 150 μL) was added and stirring continued for 1 h. At this time TLC showed mainly the amide and ester, hence few drops of acetic acid were added, stirring continued for 10 minutes. The solution was concentrated and purified in a 12 silica cartridge. The amide was obtained as light brown solids (5 mg). Data: $^1$H NMR (600 MHz, DMSO-$d_6$) δ ppm 6.68-6.75 (m, 1H) 7.38 (d, J=3.22 Hz, 1H) 7.49 (br. s., 2H) 7.61 (t, J=7.76 Hz, 1H) 7.90 (s, 1H) 7.96 (d, J=7.91 Hz, 1H) 8.00-8.18 (m, 7H) 8.24 (s, 1H) 8.43 (d, J=8.49 Hz, 1H) 8.68 (s, 1H). ESI (m/z)=(M+H) 384.

Synthesis of CG-RS-90

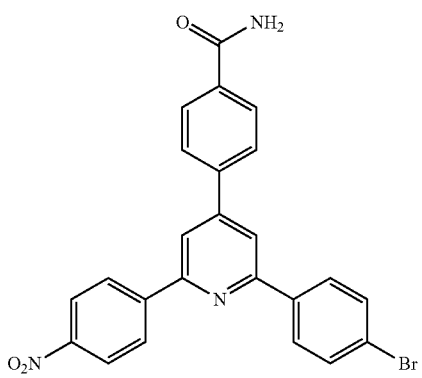

The solids CG-RS-86 (1.54 g, 4.7 mmol) and CG-RS-87 (1.67 g, 5.17 mmol) were taken in a RB flask under nitrogen. DMF (30 mL) was added, followed by acetic acid (15 mL) and then NH$_4$OAc (~9 g, 118 mmol) was added. Placed in a preheated oil bath at 50° C. and then heated to 90° C., maintained at this temperature for 3 h. At this time, LC showed mainly the desired product. Heating off, allowed to cool down to room temperature. Quenched by adding excess water, and stirred for a while. Solids separate out and filtered and washed with water several times, dried, reddish brown solids 1.76 g. The crude material 125 mg was taken in DCM (1 mL) and loaded on to a 12 g silica gel cartridge. The column was eluted with 100% DCM till 10 minutes, 0-5% MeOH/DCM from 10-25 minutes and 5% MeOH/DCM from 25-30 minutes. The product was obtained as light brown solids (45 mg). Data: $^1$H NMR (599 MHz, DMSO-$d_6$) δ ppm 7.47 (s, 1H) 7.71-7.75 (m, 2H) 7.91 (s, 1H) 8.04 (d, J=8.49 Hz, 2H) 8.11 (br. s., 1H) 8.17 (d, J=8.49 Hz, 2H) 8.32 (d, J=8.49 Hz, 2H) 8.34-8.40 (m, 3H) 8.44 (s, 1H) 8.61 (d, J=9.08 Hz, 2H). ESI (m/z)=(M+H) 474.

Synthesis of CG-RS-91

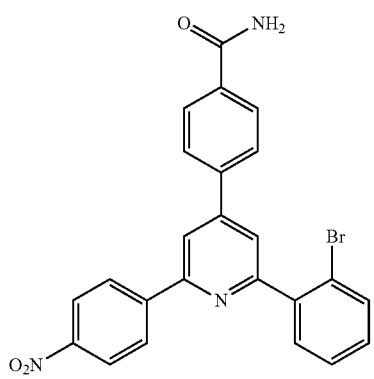 [SMILES: NC(=O)c1ccc(-c2cc(-c3ccc([N+](=O)[O-])cc3)nc(-c3ccccc3Br)c2)cc1]

The solids CG-RS-89 (1.54 g, 4.7 mmol) and CG-RS-87 (1.67 g, 5.17 mmol) were taken in a RB flask under nitrogen. DMF (30 mL) was added, followed by acetic acid (15 mL) and then NH$_4$OAc (~9 g, 118 mmol) was added. Placed in a preheated oil bath at 50° C. and then heated to 90° C., maintained at this temperature for 3 h. At this time, LC showed mainly the desired product. Heating off, allowed to cool down to room temperature. The workup and purification as described in CG-RS-90. Data: NMR (599 MHz, DMSO-$d_6$) δ ppm 7.41 (td, J=7.69, 1.61 Hz, 1H) 7.46 (s, 1H) 7.54 (t, J=7.47 Hz, 1H) 7.73 (dd, J=7.61, 1.46 Hz, 1H) 7.79 (d, J=8.20 Hz, 1H) 8.03 (d, J=7.61 Hz, 3H) 8.06-8.14 (m, 3H) 8.34 (d, J=9.08 Hz, 2H) 8.48 (d, J=1.17 Hz, 1H) 8.55 (d, J=8.78 Hz, 2H). ESI (m/z) (M+H) 474.

Synthesis of CG-RS-106

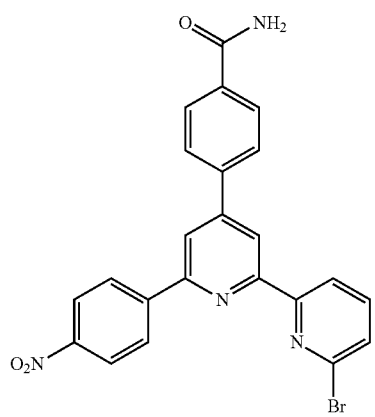 [SMILES: NC(=O)c1ccc(-c2cc(-c3ccc([N+](=O)[O-])cc3)nc(-c3cccc(Br)n3)c2)cc1]

The solids CG-RS-105 (650 mg, 1.96 mmol) and CG-RS-87 (698 mg, 2.2 mmol) were taken in a RB flask under nitrogen. DMF (12 mL) was added, followed by acetic acid (6 mL) and then NH$_4$OAc (3.8 g, 49 mmol) was added. Placed in a preheated oil bath at 50° C. and then heated to 90° C., maintained at this temperature for 3 h. At this time, LC showed mainly the desired product. Heating off, allowed to cool down to room temperature. Quenched by adding excess water, and stirred for a while. Solids separate out, filtered and washed with water several times, washed with diethyl ether multiple times, dried. The solids were purified in a 40 g silica cartridge as described before. Data: $^1$H NMR (599 MHz, DMSO-$d_6$) μ ppm 7.25-7.35 (m, 1H) 7.47 (br. s., 1H) 7.77 (d, J=7.61 Hz, 1H) 7.97 (t, J=7.76 Hz, 1H) 8.03-8.14 (m, 5H) 8.36 (d, J=8.78 Hz, 2H) 8.54 (s, 2H) 8.59-8.68 (m, 2H). ESI (m/z)=(M+H) 475.

Synthesis of CG-RS-109

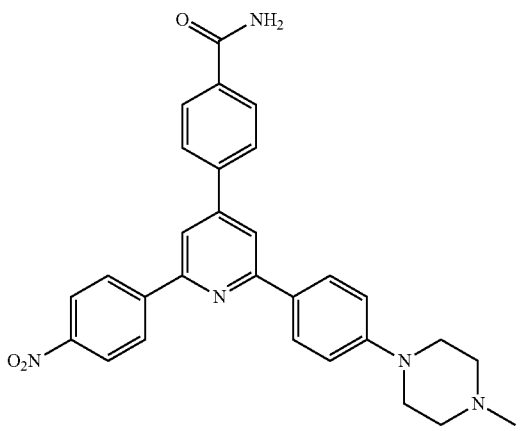 [SMILES: CN1CCN(c2ccc(-c3cc(-c4ccc(C(N)=O)cc4)cc(-c4ccc([N+](=O)[O-])cc4)n3)cc2)CC1]

The following were taken in a microwave reaction vessel, CG-RS-90 (120 mg, 0.25 mmol), N-methylpiperazine (70 μL, 0.625 mmol), BINAP (31 mg, 0.05 mmol), and dioxane (3 mL) under inert atmosphere at room temperature. NaO$^t$bu (60 mg, 0.625 mmol) was added followed by catalyst Pd$_2$dba$_3$ (23 mg, 0.025 mmol), the resulting dark reddish solution was subjected to vacuum and pressure cycles using nitrogen for three times. Placed in a microwave reactor and heated to 105° C. for 4 h, 2 mL of DMF was added to the dark solution and filtered, rinsed with 20% MeOH/DCM (10 mL×3), the filtrate was concentrated and purified in a 40 g silica cartridge. The product was obtained in poor yield, 5 mg. Data: HPLC RT=3.66, ESI (m/z)=(M+H) 494.

Synthesis of CG-RS-115

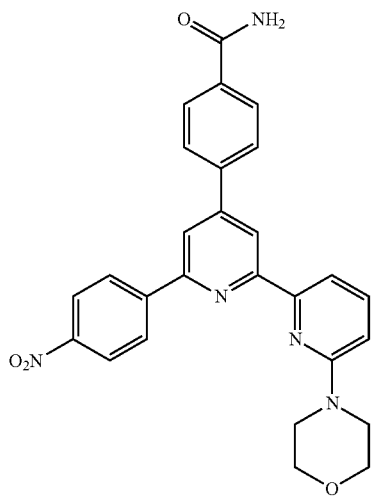 [SMILES: NC(=O)c1ccc(-c2cc(-c3ccc([N+](=O)[O-])cc3)nc(-c3cccc(N4CCOCC4)n3)c2)cc1]

The following were taken in a microwave reaction vessel, CG-RS-106 (120 mg, 0.25 mmol), morpholine (55 μL, 0.625 mmol), BINAP (31 mg, 0.05 mmol), and dioxane (4.5 mL) under inert atmosphere at room temperature. NaO$^t$bu (60 mg, 0.625 mmol) was added followed by Pd$_2$dba$_3$ (23 mg, 0.025 mmol), the resulting dark reddish solution was subjected to vacuum and pressure cycles using nitrogen for three times. Placed in a microwave reactor and heated to 105° C. for 4 h, 2 mL of DMF was added to the dark solution and filtered, rinsed with 20% MeOH/DCM (10 mL×3), the filtrate was concentrated and purified in a 40 g silica cartridge. The product was obtained in poor yield, 4 mg as light yellow solids. Data: HPLC RT=4.22, ESI (m/z)=(M+H) 482.

Synthesis of CG-RS-116

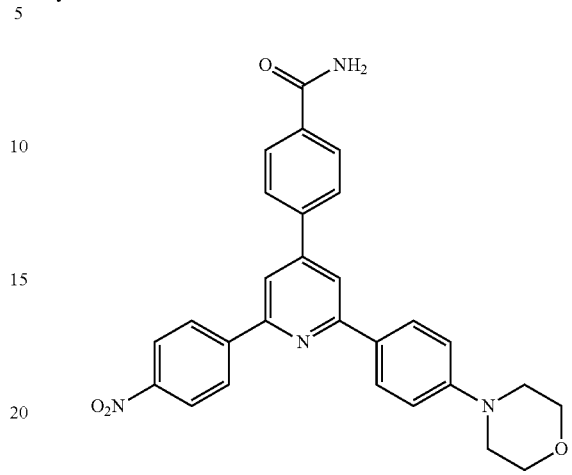

The following were taken in a dry two-neck RB flask, CG-RS-90 (120 mg, 0.25 mmol), morpholine (55 μL, 0.625 mmol), BINAP (31 mg, 0.05 mmol), and dioxane (5 mL) under inert atmosphere at room temperature. NaO$^t$bu (60 mg, 0.625 mmol) was added followed by catalyst Pd$_2$dba$_3$ (23 mg, 0.025 mmol), the resulting dark reddish solution was subjected to vacuum and pressure cycles using nitrogen for three times. Heated to 100° C. for 36 h, heating off, allowed to cool down to room temperature. The reaction contents were filtered through a pad of celite, rinsed with DCM (30 mL), ethyl acetate (30 mL) and 1:1 DCM/EA (30 mL). The filtrate were concentrated and purified in a 12 g silica cartridge. The product 16 mg was obtained as light yellow solids. Data: $^1$H NMR (599 MHz, DMSO-d$_6$) δ ppm 3.19-3.24 (m, 4H) 3.71-3.79 (m, 4H) 7.07 (d, J=8.78 Hz, 2H) 7.45 (s, 1H) 8.03 (d, J=8.49 Hz, 3H) 8.13 (d, J=8.20 Hz, 4H) 8.21-8.27 (m, 4H) 8.29 (s, 1H) 8.36 (d, J=9.08 Hz, 3H) 8.60 (d, J=9.08 Hz, 2H). ESI (m/z)=(M+H) 481.

Synthesis of CG-RS-123

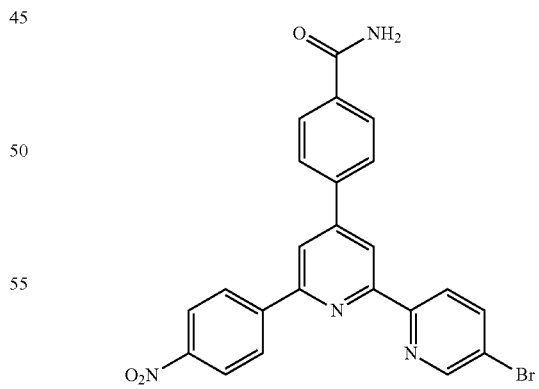

The solids CG-RS-121 (1.3 g, 3.9 mmol) and CG-RS-87 (1.4 g, 4.3 mmol) were taken in a RB flask under nitrogen. DMF (20 mL) was added, followed by acetic acid (10 mL) and then NH$_4$OAc (7.5 g, 97.5 mmol) was added. Placed in a preheated oil bath at 50° C. and then heated to 90° C., maintained at this temperature for 3 h. At this time, LC showed mainly the desired product. Heating off, allowed to cool down to room temperature. Quenched by adding excess water, and stirred for a while. Solids separate out and filtered and washed with water several times, dried, tan solids. The crude material 250 mg was taken in a mixture of DCM/MeOH/DMF (~1 mL) and loaded on to a 40 g silica gel cartridge. The column was eluted with 100% DCM till 5 minutes, 0-5% MeOH/DCM from 5-25 minutes and 5% MeOH/DCM from 25-32 minutes. The product was obtained as light brown solids (38 mg). Data: $^1$H NMR (599 MHz, DMSO-d$_6$) □ ppm 7.47 (br. s., 1H) 8.01-8.14 (m, 5H) 8.26 (dd, J=8.49, 2.05 Hz, 1H) 8.36 (d, J=8.49 Hz, 2H) 8.50-8.58 (m, 2H) 8.60-8.68 (m, 3H) 8.86 (d, J=2.05 Hz, 1H). ESI (m/z)=(M+H) 475.

Synthesis of CG-RS-125

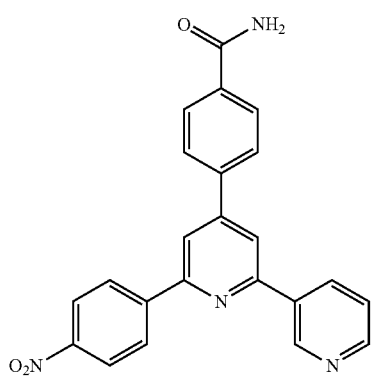 [SMILES: NC(=O)c1ccc(-c2cc(-c3ccc([N+](=O)[O-])cc3)nc(-c3cccnc3)c2)cc1]

The solids CG-RS-122 (100 mg, 0.39 mmol) and CG-RS-87 (140 mg, 0.43 mmol) were taken in a RB flask under nitrogen. DMF (3 mL) was added, followed by acetic acid (1.5 mL) and then NH$_4$OAc (800 mg, 10.4 mmol) was added. Placed in a preheated oil bath at 50° C. and then heated to 90° C., maintained at this temperature for 3 h. At this time, LC showed mainly the desired product. Heating off, allowed to cool down to room temperature. Quenched by adding excess water, and stirred for a while. Solids separate out and filtered and washed with water several times, dried, end up a dark residue. The residue was treated with a mixture of DCM/MeOH, filtered, rinsed with the same solvent system several times. Concentrated and purified in a 12 g silica cartridge, 24 mg of the desired product was obtained as brown solids. Data: $^1$H NMR (599 MHz, DMSO-d$_6$) δ ppm 6.79 (br. s., 1H) 7.04 (br. s., 1H) 7.48 (br. s., 1H) 7.58 (dd, J=7.76, 4.83 Hz, 1H) 8.06 (d, J=8.20 Hz, 2H) 8.12 (br. s., 1H) 8.20 (d, J=8.20 Hz, 2H) 8.37 (d, 1=8.49 Hz, 2H) 8.48 (d, J=13.47 Hz, 2H) 8.61-8.74 (m, 3H) 9.53 (s, 1H). ESI (m/z)=(M+H) 397.

Synthesis of CG-RS-128

The solids CG-RS-124 (252 mg, 1 mmol) and CG-RS-87 (355 mg, 1.1 mmol) were taken in a RB flask under nitrogen. DMF (8 mL) was added, followed by acetic acid (4 mL) and then NH$_4$OAc (1.93 g, 25 mmol) was added. Placed in a preheated oil bath at 50° C. and then heated to 90° C., maintained at this temperature for 3 h. At this time, LC showed mainly the desired product. Heating off, allowed to cool down to room temperature. Similar workup and purification procedure as described in CG-RS-125 led to the target compound. Data: $^1$H NMR (599 MHz, DMSO-d$_6$) δ ppm 7.47 (br. s., 1H) 7.52 (d, J=12.30 Hz, 1H) 7.99-8.15 (m, 6H) 8.38 (d, J=8.78 Hz, 2H) 8.53 (s, 1H) 8.63 (d, J=7.91 Hz, 1H) 8.66 (d, J=8.78 Hz, 2H) 8.71-8.77 (m, 2H). EST (m/z)=(M+H) 397.

Synthesis of CG-RS-129

The solids CG-RS-127 (252 mg, 1 mmol) and CG-RS-87 (355 mg, 1.1 mmol) were taken in a RB flask under nitrogen. DMF (8 mL) was added, followed by acetic acid (4 mL) and then NH$_4$OAc (1.93 g, 25 mmol) was added. Placed in a preheated oil bath at 50° C. and then heated to 90° C., maintained at this temperature for 3 h. At this time, LC showed mainly the desired product. Heating off, allowed to cool down to room temperature. Similar workup and purification procedure as described in CG-RS-125 led to the target compound. Data: HPLC RT=3.46, ESI (m/z)=(M+H) 397.

Synthesis of CG-RS-130

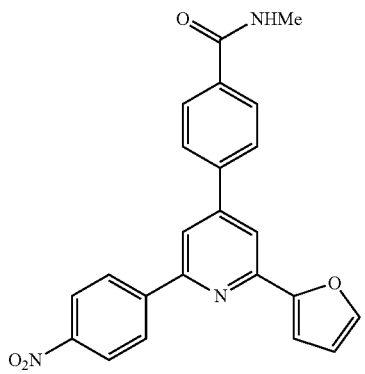 [SMILES: CNC(=O)c1ccc(-c2cc(-c3ccc([N+](=O)[O-])cc3)nc(-c3ccco3)c2)cc1]

The solids CG-RS-44 (100 mg, 0.26 mmol) was taken in DMF (3 mL) at 0° C. under nitrogen. After few minutes of stirring, NaH (16 mg, 60% dispersion, 0.39 mmol) was added, stirring continued for 5 minutes, at this time MeI (16 µL, 0.26 mmol) was added. Stirring continued while warming up to room temperature. After 2 h, TLC showed three spots including the starting material. Quenched with water, usual work up and purification led to the desired product (7 mg). Data: $^1$H NMR (599 MHz, DMSO-$d_6$) δ ppm 2.80 (d, J=4.10 Hz, 3H) 6.72 (br. s., 1H) 7.39 (d, J=3.22 Hz, 1H) 7.89-7.94 (m, 1H) 8.00 (d, J=8.20 Hz, 2H) 8.08-8.16 (m, 3H) 8.32-8.41 (m, 3H) 8.58 (d, J=8.20 Hz, 3H). ESI (m/z)=(M+H) 400.

Synthesis of CG-RS-131

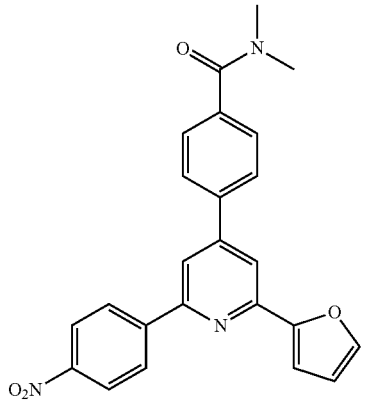 [SMILES: CN(C)C(=O)c1ccc(-c2cc(-c3ccc([N+](=O)[O-])cc3)nc(-c3ccco3)c2)cc1]

The solids CG-RS-44 (193 mg, 0.5 mmol) was taken in DMF (6 mL) at 0° C. under nitrogen. After few minutes of stirring, NaH (96 mg, 60% dispersion, 2 mmol) was added, stirring continued for 5 minutes, at this time MeI (125 µL, 2 mmol) was added. Stirring continued while warming up to room temperature. After overnight stirring, TLC showed mainly single spot. Quenched with water, usual work up gave 170 mg of crude product, out of which 50 mg was purified and the rest taken to next step. Data: $^1$H NMR (599 MHz, DMSO-$d_6$) δ ppm 2.84-3.09 (m, 6H) 6.72 (br. s., 1H) 7.39 (d, J=3.22 Hz, 1H) 7.57 (d, J=7.91 Hz, 2H) 7.91 (s, 1H) 7.99-8.16 (m, 3H) 8.26-8.44 (m, 3H) 8.57 (d, J=8.49 Hz, 2H). ESI (m/z)=(M+H) 414.

Synthesis of CG-RS-134

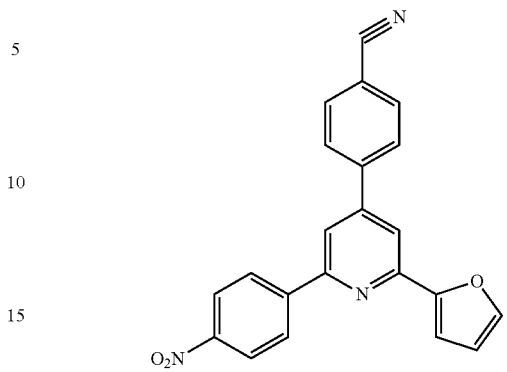

CG-RS-44 (77 mg, 0.2 mmol) was taken in DCM (2 mL) at room temperature under nitrogen. After few minutes of stirring, TFAA (44 µL) was added followed by TEA (60 µL). After stirring for 2 h at room temperature, TLC and LC both showed the desired product. DCM was added and then water, the layers were separated. The aqueous layer was extracted with DCM, the combined organic portion was washed with water twice, dried (Na$_2$SO$_4$). The crude product was purified in a 12 g silica cartridge to obtain 43 mg of desired compound as yellow solids. Data: $^1$H NMR (599 MHz, DMSO-$d_6$) δ ppm 6.72 (br. s., 1H) 7.40 (d, J=3.22 Hz, 1H) 7.92 (s, 1H) 8.03 (d, J=8.20 Hz, 2H) 8.11 (s, 1H) 8.22 (d, J=8.20 Hz, 2H) 8.31-8.41 (m, 3H) 8.57 (d, J=8.49 Hz, 2H). ESI (m/z)=(M+H) 368.

Synthesis of CG-RS-136

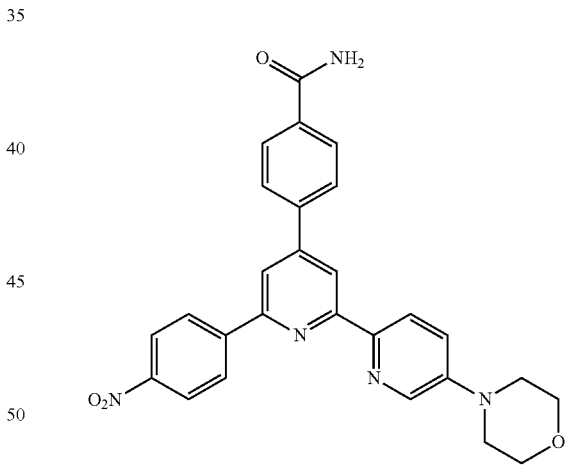

The following were taken in a dry two-neck RB flask, CG-RS-123 (240 mg, 0.5 mmol), morpholine (109 µL, 1.25 mmol), BINAP (62 mg, 0.1 mmol), and dioxane (7 mL) under inert atmosphere at room temperature. NaO$^t$bu (120 mg, 1.25 mmol) was added followed by catalyst Pd$_2$dba$_3$ (46 mg, 0.05 mmol), the resulting dark reddish solution was subjected to vacuum and pressure cycles using nitrogen for three times. Heated to 100° C. for 24 h, heating off, allowed to cool down to room temperature. The reaction contents were filtered through a cotton plug, rinsed with mixture of DCM/MeOH several times. The filtrate were concentrated, dissolved in DMF (2 mL) and purified in a 40 g silica cartridge. The product 32 mg was obtained as yellow solids. Data: $^1$H NMR (599 MHz, DMSO-$d_6$) δ ppm 3.28-3.51 (m, 4H) 3.76 (br. s., 4H) 6.64-7.16 (m, 1H) 7.36-7.60 (m, 2H) 8.05 (s, 5H) 8.30-8.52 (m, 4H) 8.52-8.69 (m, 2H). ESI (m/z)=(M+H) 482.

Synthesis of CG-RS-137

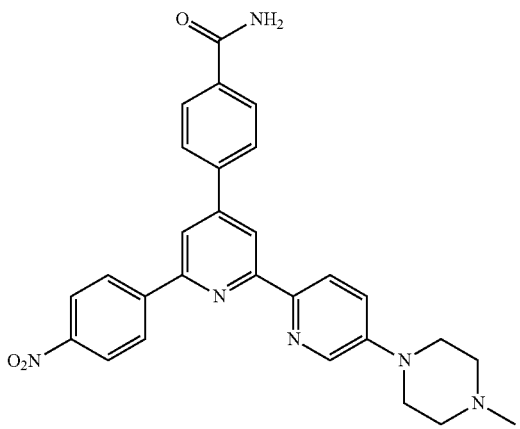

The following were taken in a dry two-neck RB flask, CG-RS-123 (240 mg, 0.5 mmol), N-methylpiperazine(139 µL, 1.25 mmol), BINAP (62 mg, 0.1 mmol), and dioxane (7 mL) under inert atmosphere at room temperature. NaO$^t$bu (120 mg, 1.25 mmol) was added followed by catalyst Pd$_2$dba$_3$ (46 mg, 0.05 mmol), the resulting dark reddish solution was subjected to vacuum and pressure cycles using nitrogen for three times. Heated to 100° C. for 24 h, heating off, allowed to cool down to room temperature. The reaction contents were filtered through a cotton plug, rinsed with mixture of DCM/MeOH several times. The filtrate were concentrated, dissolved in DMF (2 mL) and purified in a 40 g silica cartridge. The product 28 mg was obtained as yellow solids. Data: $^1$H NMR (599 MHz, DMSO-d$_6$) δ ppm 2.33 (br. s., 3H) 2.61 (br. s., 4H) 3.32-3.41 (m, 4H) 7.45 (br. s., 1H) 7.51 (d, J=2.34 Hz, 1H) 8.05 (s, 4H) 8.10 (br. s., 1H) 8.33-8.40 (m, 3H) 8.41-8.47 (m, 2H) 8.55-8.65 (m, 3H). ESI (m/z)=(M+H) 495.

Synthesis of CG-RS-143

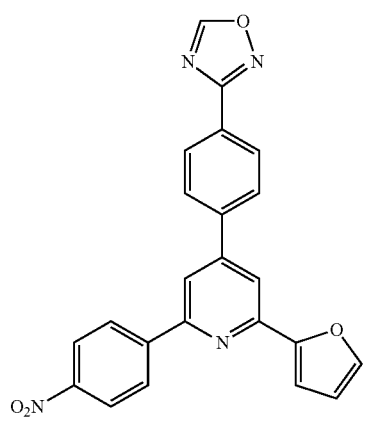 [SMILES: O=[N+]([O-])c1ccc(-c2cc(-c3ccc(-c4ncon4)cc3)cc(-c3ccco3)n2)cc1]

The following were taken in a dry RB flask, NH$_4$OH.HCl (70 mg, 1 mmol) and K$_2$CO$_3$ (276 mg, 2 mmol) in ethanol (3 mL).Stirred for 5 minutes and then CG-RS-140 (100 mg, 0.27 mmol) was added and then heated to reflux. After 6 h of reflux, the reaction mixture was concentrated in a rotary evaporator. MeOH was added, filtered and then rinsed with more MeOH, concentrated. To the residue was added triethyl orthoformate (~5 mL) and heated to 140-150° C. overnight. Heating off, allowed to cool down and concentrated. The residue was purified in a 12 g silica cartridge; ~3 mg of the desired product was obtained. Data: HPLC RT=4.32, ESI (m/z)=(M+H) 411.

Synthesis of CG-RS-147

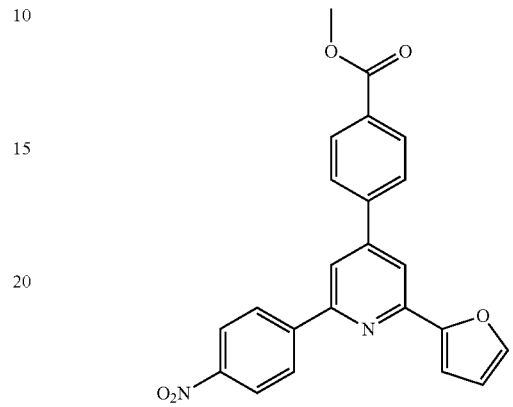

The solids CG-RS-145 (512 mg, 2 mmol) and CG-RS-87 (711 mg, 2.2 mmol) were taken in a RB flask under nitrogen. DMF (10 mL) was added, followed by acetic acid (5 mL) and then NH$_4$OAc (4.6 g, 60 mmol) was added. Placed in a preheated oil bath at 50° C. and then heated to 90° C., maintained at this temperature for 3 h. At this time, LC showed mainly the desired product. Heating off, allowed to cool down to room temperature. Quenched by adding excess water, and stirred for a while. Solids separate out and filtered and washed with water several times, dried. The solids were dissolved in DCM (10 mL) and silica gel (8 g) was added, concentrated. The solids were loaded on to a silica gel plug and purified. The product was obtained as yellow solids (330 mg). Data: $^1$H NMR (599 MHz, DMSO-d$_6$) δ ppm 3.88 (s, 3H) 6.71 (dd, J=3.22, 1.76 Hz, 1H) 7.38 (d, J=3.22 Hz, 1H) 7.91 (s, 1H) 8.03-8.21 (m, 5H) 8.35 (d, J=9.66 Hz, 3H) 8.56 (d, J=8.78 Hz, 2H). ESI (m/z)=(M+H) 401.

Synthesis of CG-RS-148

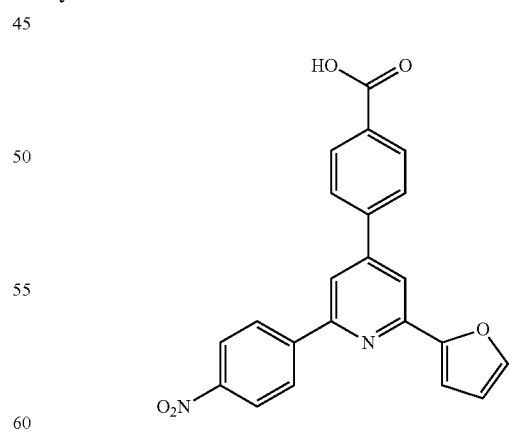

The solids CG-RS-147 (60 mg, 0.15 mmol) was taken in THF (3 mL) and the 1 M aqueous LiOH (0.3 mL, 0.3 mmol) was added. The resulting solution was stirred at room temperature overnight. At this time LC showed only the starting material and hence another portion of 1 M aqueous LiOH (0.3 mL, 0.3 mmol) was added. Heated to 50° C. for 3 h. At this time TLC showed no starting material remains, hence heating off Allowed to cool down to room temperature. Ethyl acetate and water were added, the layers were separated. The aqueous layer was washed with ethyl acetate, then acidified to pH-5. Extracted with DCM twice, since both organic layers have compounds, combined, dried and concentrated. Purified in a 12 g silica cartridge to obtain 32 mg of the desired compound as white solids. Data: $^1$H NMR (599 MHz, DMSO-$d_6$) δ ppm 6.71 (dd, 0.1=3.22, 1.46 Hz, 1H) 7.39 (d, J=3.22 Hz, 1H) 7.91 (s, 1H) 8.02-8.20 (m, 5H) 8.28-8.42 (m, 3H) 8.57 (d, J=8.78 Hz, 2H) 13.15 (br. s., 1H). ESI (m/z)=(M+H) 387.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, ATCC deposits, patents and patent applications cited herein are hereby expressly incorporated by reference in their entirety and for all purposes as if each is individually so denoted.

We claim:

1. A method of treating c-Myc driven cancer, comprising administering an effective amount of 4-(2-(furan-2-yl)-6-(4-nitrophenyl)pyridin-4-yl)benzamide (CG-RS-44).

* * * * *